United States Patent
Schaefer et al.

(10) Patent No.: US 10,470,857 B2
(45) Date of Patent: Nov. 12, 2019

(54) PERSONAL CARE DEVICE

(75) Inventors: Norbert Schaefer, Frankfurt am Main (DE); Uwe Schober, Schlossborn (DE); Joern Utsch, Eschborn (DE); Andreas Kramp, Bad Camberg (DE); Frank Ziegler, Karben (DE); Benedikt Heil, Friedberg (DE); Marlis Hübner, Schwalbach an Taunus (DE)

(73) Assignee: Braun GmbH, Kronberg (DE)

( * ) Notice: Subject to any disclaimer, the term of this patent is extended or adjusted under 35 U.S.C. 154(b) by 305 days.

(21) Appl. No.: 13/190,293

(22) Filed: Jul. 25, 2011

(65) Prior Publication Data
US 2012/0036658 A1 Feb. 16, 2012

(30) Foreign Application Priority Data

Jul. 23, 2010 (EP) .................................... 10007716

(51) Int. Cl.
*A61C 17/34* (2006.01)
*H02K 33/10* (2006.01)
*A61C 17/22* (2006.01)

(52) U.S. Cl.
CPC ........ *A61C 17/222* (2013.01); *A61C 17/3436* (2013.01); *H02K 33/10* (2013.01)

(58) Field of Classification Search
CPC ......... A46B 13/02; A61C 17/22; A61C 17/32; A61C 17/34; A61C 17/3409; A61C 17/3436
USPC .......................................... 15/22.1, 22.2, 28
See application file for complete search history.

(56) References Cited

U.S. PATENT DOCUMENTS

| | | | |
|---|---|---|---|
| 2,598,275 A | * | 5/1952 | Lakin ................................ 74/36 |
| 4,374,354 A | | 2/1983 | Petrovic et al. |
| 4,420,851 A | | 12/1983 | Wiener |
| 4,502,497 A | | 3/1985 | Siahou |
| 4,595,849 A | | 6/1986 | Cuenoud |
| 4,603,448 A | | 8/1986 | Middleton et al. |
| 5,165,131 A | | 11/1992 | Staar |
| 5,168,186 A | | 12/1992 | Yashiro |
| 5,189,751 A | | 3/1993 | Giuliani et al. |
| 5,259,083 A | | 11/1993 | Stansbury, Jr. |
| 5,263,218 A | | 11/1993 | Giuliani et al. |

(Continued)

FOREIGN PATENT DOCUMENTS

| | | |
|---|---|---|
| AU | 2005100387 A4 | 5/2005 |
| CH | 688 537 A5 | 11/1997 |

(Continued)

OTHER PUBLICATIONS

Partial machine translation of JP 2002-45379, Feb. 12, 2002.*
PCT International Search Report dated Nov. 2, 2011.

*Primary Examiner* — Mark Spisich
(74) *Attorney, Agent, or Firm* — George H. Leal; Amanda T. Barry

(57) ABSTRACT

A personal care device having a handle having an engagement portion and a persona care attachment are described. The personal care attachment has a housing attached to the engagement portion and a contact element carrier. The contact element carrier is movably coupled to the housing. A plurality of contact elements is arranged on the contact element carrier, and wherein the personal care attachment is driven at a frequency of between about 150 Hz to about 175 Hz and has a sound intensity level of less than about 75 dB(A).

7 Claims, 18 Drawing Sheets

(56) References Cited

U.S. PATENT DOCUMENTS

| | | |
|---|---|---|
| 5,274,735 A | 12/1993 | Okada |
| 5,309,590 A | 5/1994 | Giuliani et al. |
| 5,367,599 A | 11/1994 | Okada |
| 5,378,153 A | 1/1995 | Giuliani et al. |
| 5,476,384 A | 12/1995 | Giuliani et al. |
| 5,561,881 A | 10/1996 | Klinger et al. |
| 5,613,259 A | 3/1997 | Craft et al. |
| 5,617,503 A | 4/1997 | Fronen et al. |
| 5,617,601 A | 4/1997 | McDougall |
| 5,673,451 A | 10/1997 | Moore et al. |
| 5,700,146 A | 12/1997 | Kucar |
| 5,781,955 A | 7/1998 | Hendricks |
| 5,784,742 A | 7/1998 | Giuliani et al. |
| 5,799,356 A | 9/1998 | Kawashima |
| 5,934,908 A | 8/1999 | Woog et al. |
| 5,955,799 A | 9/1999 | Amaya et al. |
| 5,974,615 A | 11/1999 | Schwarz-Hartmann |
| 5,994,855 A | 11/1999 | Lundell et al. |
| 6,021,538 A | 2/2000 | Kressner et al. |
| 6,133,701 A | 10/2000 | Gokturk et al. |
| 6,140,802 A | 10/2000 | Lundell et al. |
| 6,227,853 B1 | 5/2001 | Hansen et al. |
| 6,322,573 B1 | 11/2001 | Murayama |
| 6,441,571 B1 | 8/2002 | Ibuki et al. |
| 6,498,456 B2 | 12/2002 | Ettes et al. |
| 6,517,348 B1 | 2/2003 | Ram |
| 6,538,402 B2 | 3/2003 | Gokturk et al. |
| 6,716,028 B2 | 4/2004 | Rahman et al. |
| 6,760,945 B2 | 7/2004 | Ferber et al. |
| 6,766,824 B2 | 7/2004 | Taylor |
| 6,811,399 B2 | 11/2004 | Rahman et al. |
| 6,845,537 B2 | 1/2005 | Wong |
| 6,859,968 B2 | 3/2005 | Miller et al. |
| 6,873,067 B2 | 3/2005 | Ichii et al. |
| 6,891,287 B2 | 5/2005 | Moret |
| 6,895,630 B2 | 5/2005 | Tini |
| 6,918,300 B2 | 7/2005 | Grez et al. |
| 6,954,961 B2 | 10/2005 | Ferber et al. |
| 6,958,553 B2 | 10/2005 | Ichii et al. |
| 6,964,076 B2 | 11/2005 | Zhuan |
| 7,011,520 B2 | 3/2006 | Rahman et al. |
| 7,086,111 B2 | 8/2006 | Hilscher et al. |
| 7,194,862 B2 | 3/2007 | Sattinger |
| 7,307,397 B2 | 12/2007 | Izumi et al. |
| 7,315,098 B2 | 1/2008 | Kunita et al. |
| 7,334,283 B2 | 2/2008 | Kunita et al. |
| 7,409,741 B2 | 8/2008 | Dworzan |
| 7,443,058 B2 | 10/2008 | Shimizu et al. |
| 7,469,703 B2 | 12/2008 | France et al. |
| 7,474,018 B2 | 1/2009 | Shimizu et al. |
| 7,474,065 B2 | 1/2009 | Kraus |
| 7,493,669 B2 | 2/2009 | Miller et al. |
| 7,495,358 B2 | 2/2009 | Kobayashi et al. |
| 7,535,135 B2 | 5/2009 | Kardeis et al. |
| 7,627,922 B2 | 12/2009 | Miller et al. |
| 7,654,271 B2 | 2/2010 | Wyatt et al. |
| 7,687,944 B2 | 3/2010 | Benning et al. |
| 7,712,174 B2 | 5/2010 | Shimizu et al. |
| 7,784,144 B2 | 8/2010 | Renault |
| 7,861,349 B2 | 1/2011 | Hilscher et al. |
| 7,876,003 B2 | 1/2011 | Bax |
| 7,979,938 B2 | 7/2011 | Lilley et al. |
| 7,979,939 B2 | 7/2011 | Hilscher et al. |
| 8,015,648 B2 | 9/2011 | Hall |
| 2002/0084707 A1 | 7/2002 | Tang |
| 2002/0127512 A1 | 9/2002 | Chen et al. |
| 2002/0195884 A1 | 12/2002 | Ichii et al. |
| 2003/0000032 A1 | 1/2003 | Lev |
| 2004/0068811 A1 | 4/2004 | Fulop et al. |
| 2004/0128778 A1 | 7/2004 | Wong |
| 2004/0130221 A1 | 7/2004 | Ichii et al. |
| 2004/0168269 A1 | 9/2004 | Kunita et al. |
| 2004/0191724 A1 | 9/2004 | Rahman et al. |
| 2005/0011022 A1 | 1/2005 | Kwong |
| 2005/0037316 A1 | 2/2005 | Sholder |
| 2005/0050658 A1 | 3/2005 | Chan et al. |
| 2005/0125919 A1 | 6/2005 | Fattori |
| 2005/0199265 A1 | 9/2005 | France et al. |
| 2005/0235438 A1 | 10/2005 | Motohashi et al. |
| 2005/0278877 A1 | 12/2005 | Akridge et al. |
| 2006/0254007 A1 | 11/2006 | Banning |
| 2006/0272667 A1 | 12/2006 | Wyatt et al. |
| 2007/0000079 A1 | 1/2007 | Mori et al. |
| 2008/0102419 A1 | 5/2008 | Sauter et al. |
| 2008/0196735 A1 | 8/2008 | Wyatt et al. |
| 2008/0293009 A1 | 11/2008 | Winston |
| 2008/0307591 A1 | 12/2008 | Farrell et al. |
| 2009/0025156 A1 | 1/2009 | Asada et al. |
| 2009/0070947 A1 | 3/2009 | Baertschi et al. |
| 2009/0091275 A1 | 4/2009 | Miller et al. |
| 2009/0177125 A1 | 7/2009 | Pilcher et al. |
| 2009/0183324 A1 | 7/2009 | Fischer et al. |
| 2009/0241276 A1 | 10/2009 | Hall et al. |
| 2009/0243519 A1 | 10/2009 | Izumi et al. |
| 2009/0243520 A1 | 10/2009 | Kashiwabara et al. |
| 2009/0320221 A1 | 12/2009 | Masuko |
| 2010/0109580 A1 | 5/2010 | Lambantobing et al. |
| 2010/0132139 A1 | 6/2010 | Jungnickel |
| 2010/0263147 A1 | 10/2010 | Crossman et al. |
| 2010/0281637 A1 | 11/2010 | Hilscher et al. |
| 2010/0301783 A1 | 12/2010 | Luckel et al. |
| 2010/0306934 A1 | 12/2010 | Headstrom |
| 2011/0005015 A1 | 1/2011 | Iwahori et al. |
| 2011/0030716 A1 | 2/2011 | Lou |
| 2011/0041268 A1 | 2/2011 | Iwahori et al. |
| 2011/0041269 A1 | 2/2011 | Iwahori |
| 2011/0080061 A1 | 4/2011 | Bax |
| 2011/0080122 A1 | 4/2011 | Klemm et al. |
| 2011/0107531 A1 | 5/2011 | Ye |
| 2011/0122987 A1 | 5/2011 | Neyer |
| 2011/0138551 A1 | 6/2011 | Stopler et al. |
| 2011/0181208 A1 | 7/2011 | Murata |
| 2011/0181209 A1 | 7/2011 | Murata |
| 2011/0181211 A1 | 7/2011 | Murata |
| 2011/0203061 A1 | 8/2011 | Takahashi et al. |
| 2011/0252584 A1 | 10/2011 | Jousma et al. |
| 2011/0258793 A1 | 10/2011 | Jousma et al. |
| 2011/0273153 A1 | 11/2011 | Lepper et al. |

FOREIGN PATENT DOCUMENTS

| | | |
|---|---|---|
| CN | 1098888 A | 2/1995 |
| CN | 1520788 A | 1/2004 |
| CN | 1778278 A | 11/2004 |
| CN | 1778279 A | 11/2004 |
| CN | 1843305 A | 4/2005 |
| CN | 1846651 A | 4/2005 |
| CN | 1830403 A | 9/2006 |
| CN | 200980058 | 11/2007 |
| CN | 201055092 Y | 5/2008 |
| CN | 201403746 Y | 10/2008 |
| CN | 201295301 Y | 12/2008 |
| CN | 201187899 Y | 1/2009 |
| CN | 101427944 A | 5/2009 |
| CN | 201341578 Y | 11/2009 |
| CN | 201518881 U | 7/2010 |
| DE | 42 01 027 A1 | 7/1992 |
| DE | 94 11 158 U1 | 8/1995 |
| DE | 198 03 311 A1 | 8/1999 |
| DE | 198 40 684 A1 | 3/2000 |
| DE | 199 13 945 A1 | 9/2000 |
| DE | 201 12 320 U1 | 10/2001 |
| DE | 10 2004 029 684 A1 | 12/2005 |
| DE | 10 2005 045 800 A1 | 4/2007 |
| EP | 1 696 539 A1 | 8/2006 |
| EP | 1 733 700 B1 | 8/2010 |
| EP | 2 262 083 A1 | 12/2010 |
| GB | 2 117 230 A | 10/1983 |
| GB | 2 412 014 A | 9/2005 |
| JP | 06/01413 | 1/1994 |
| JP | 07-123600 | 5/1995 |
| JP | 07-177932 | 7/1995 |
| JP | 07-194862 | 8/1995 |
| JP | 08/066325 | 3/1996 |

(56) References Cited

FOREIGN PATENT DOCUMENTS

| | | |
|---|---|---|
| JP | 10-127346 | 5/1998 |
| JP | 10-243688 | 9/1998 |
| JP | 2001/197676 | 7/2001 |
| JP | 2001/346816 | 12/2001 |
| JP | 2002/045379 | 2/2002 |
| JP | 2002/306867 | 10/2002 |
| JP | 2002/320399 | 10/2002 |
| JP | 2003/250233 | 9/2003 |
| JP | 2003/348888 | 12/2003 |
| JP | 2004/007890 | 1/2004 |
| JP | 2006-280830 | 10/2006 |
| JP | 2009-100523 | 5/2009 |
| JP | 2010-125263 | 6/2010 |
| KR | 2003-0091408 | 12/2003 |
| KR | 10-2005-0043071 | 5/2005 |
| KR | 10-2007-0034649 | 3/2007 |
| KR | 10-0752601 | 8/2007 |
| KR | 10-2007-0107198 | 11/2007 |
| KR | 20-2008-0004243 | 10/2008 |
| KR | 10-2009-106306 | 10/2009 |
| RU | 2 077 349 C1 | 7/1993 |
| RU | 2 129 826 C1 | 5/1999 |
| SE | 531 401 C2 | 3/2009 |
| WO | WO 98/36703 A1 | 8/1998 |
| WO | WO 02/071972 A1 | 9/2002 |
| WO | WO 2005/096882 A1 | 10/2005 |
| WO | WO 2008/098107 A2 | 8/2008 |
| WO | WO 2010/106522 A1 | 9/2010 |
| WO | WO 2010/106850 A1 | 9/2010 |
| WO | WO 2010/143156 A1 | 12/2010 |
| WO | WO 2011/077289 A1 | 6/2011 |
| WO | WO 2011/077290 A1 | 6/2011 |

* cited by examiner

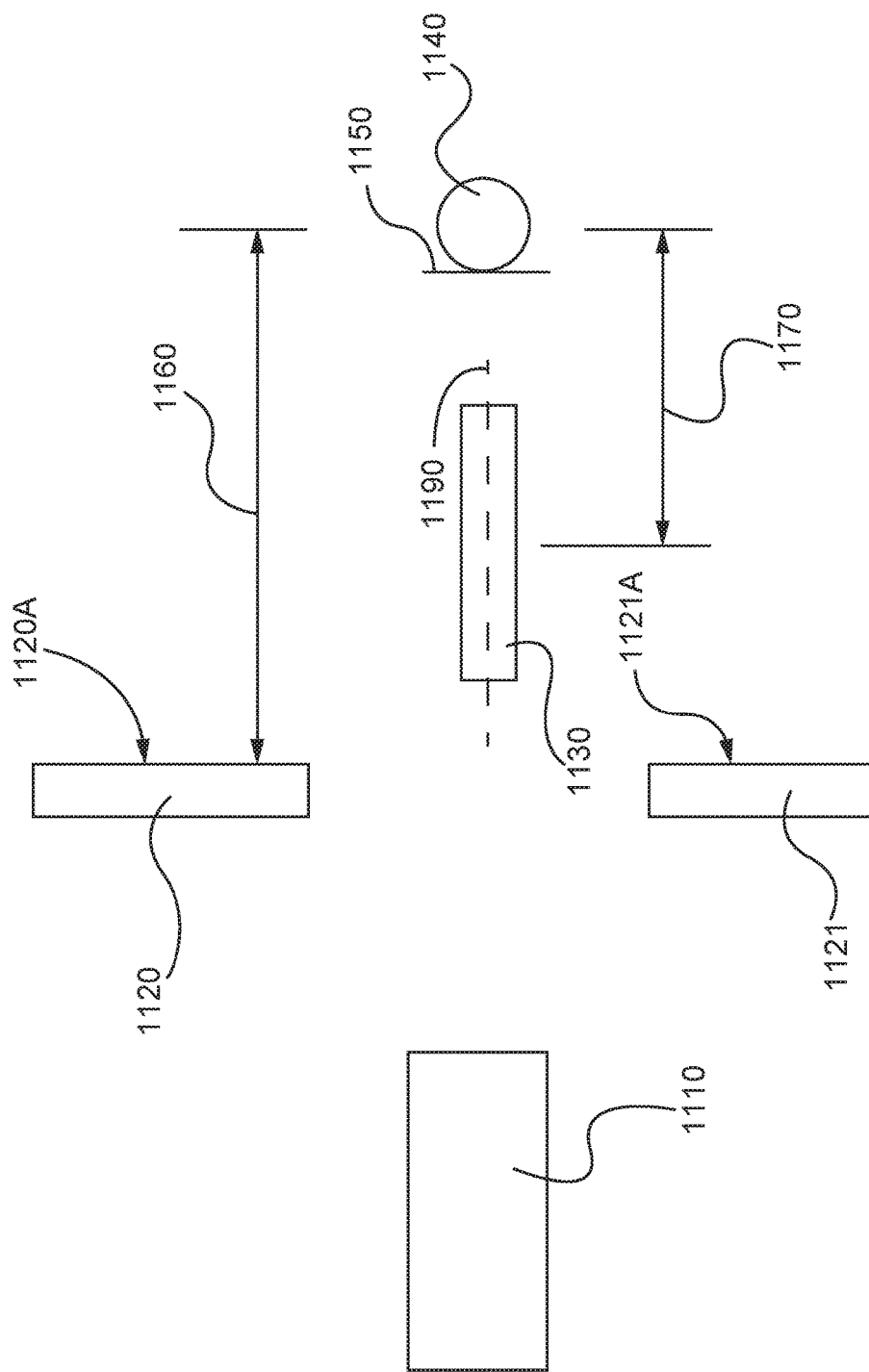

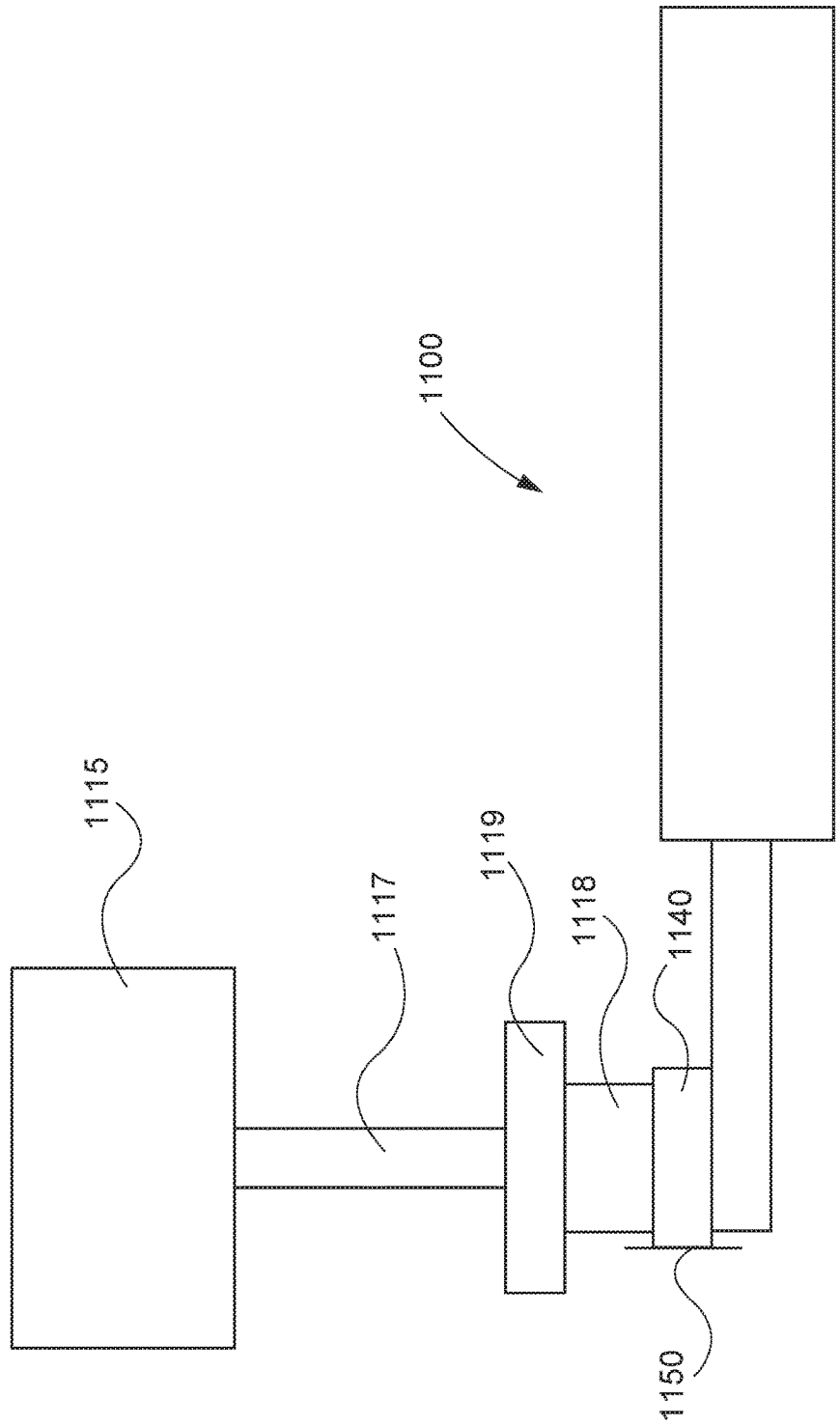

PERSONAL CARE DEVICE

FIELD OF THE INVENTION

The present invention pertains to powered personal care devices, and more particularly to powered oral care devices.

BACKGROUND OF THE INVENTION

The utilization of toothbrushes to clean one's teeth has long been known. There are generally two types of toothbrushes currently available on the market, e.g. manual and power. In general, for manual brushes, a user provides the majority of the cleaning motion to the brush in the oral cavity. In contrast, for power brushes, a motor providing a driving force to all or a portion of a head of the toothbrush provides the majority of the cleaning motion to the brush which cleans the oral cavity.

The powered toothbrush typically includes a handle having a motor and power supply therein. In general, the motors supply rotational or longitudinal energy to the refill which is attached to the handle. Normal operating speeds for powered toothbrushes can vary. For example, toothbrushes having oscillating/rotating heads, typically operate in the range of 40 Hz to 100 Hz. In contrast, some toothbrushes available on the market are termed "sonic" and can operate in the range of 160 Hz to 300 Hz. However, sonic toothbrushes do not include oscillating/rotating motion.

The drive train of the oscillating/rotating toothbrushes typically includes gearing which modifies the rotational energy of the motor. For example, many oscillating/rotating toothbrushes include a drive train which converts the 360 degress motion of a motor output shaft to a smaller oscillating angle of displacement on drive shaft. A refill couples to the drive shaft and typically modifies the direction of the rotational energy of the drive shaft. Because of these conversions of angle, displacement and/or direction, increased frequency in currently available oscillating/rotating brushes may not be realizable.

Oscillating/rotating toothbrushes with a round or oval shaped brushhead have been proven to be more efficient for the cleaning of teeth than other systems. It is believed that higher drive frequencies have the potential to further improve the mechanical cleaning offered by oscillating/rotating toothbrushes and to generate fluid dynamics effects during brushing which is believed to contribute to the cleaning. However, due to the gear systems included in the conventional oscillating/rotating toothbrushes operation at higher frequencies is limited because of the associated noise. Accordingly, conventional oscillating/rotating toothbrushes operate in the frequencies described above.

As such, there is a need for an oscillating/rotating toothbrush which can operate at frequencies greater than 100 Hz.

SUMMARY OF THE INVENTION

Embodiments of the present invention can provide a user with a personal care device which has reduced sound intensity levels. In the embodiments where the personal care device comprises a toothbrush, an oscillating/rotating toothbrush can provide the user with better cleaning and lower noise than conventional oscillating/rotating brushes.

In some embodiments, a personal care device comprises a handle having an engagement portion, and a personal care attachment. The personal care attachment comprises a housing attached to the engagement portion and a contact element carrier. The contact element carrier is movably coupled to the housing. A plurality of contact elements is arranged on the contact element carrier, wherein the personal care attachment is driven at a frequency of between about 150 Hz to about 175 Hz and has a sound intensity level of less than about 75 dB(A).

In some embodiments, a personal care attachment comprises a housing; a contact element carrier movably mounted to the housing; and a drive member disposed within the housing. The drive member has a proximal end and a distal end. The proximal end has an attachment element and the distal end comprises a connection coupled to the contact element carrier. The attachment element comprise a permanent magnet or a magnetisable material.

In some embodiments, a personal care attachment comprises a housing; a contact element carrier movably mounted to the housing; and a drive member disposed within the housing. The drive member has a proximal end and a distal end. The proximal end has an attachment element and the distal end comprises a connection coupled to the contact element carrier. The connection is positioned at an angle of less than about 40 degrees with respect to a horizontal plane.

BRIEF DESCRIPTION OF THE DRAWINGS

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The embodiments set forth in the drawings are illustrative in nature and not intended to be limiting of the subject matter defined by the claims. The drawings illustrate various embodiments described herein, and together with the description serve to explain the principles and operations of the claimed subject matter.

FIG. 11A is an elevation view of a test set up to measure oscillation displacement angle.

FIG. 11C is a plan view showing a portion of the test set up of FIG. 11A.

DETAILED DESCRIPTION OF THE INVENTION

The following text sets forth a broad description of numerous different embodiments of the present invention. The description is to be construed as exemplary only and does not describe every possible embodiment since describing every possible embodiment would be impractical, if not impossible, and it will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). No term is intended to be essential to the present invention unless so stated. To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

The personal care devices of the present invention can operate at a frequency of greater than 100 Hz. The personal care devices of the present invention may comprise shavers, razors, flossers, irrigators, etc., however, for convenience, the description below focuses primarily on toothbrushes.

Figure 1A:
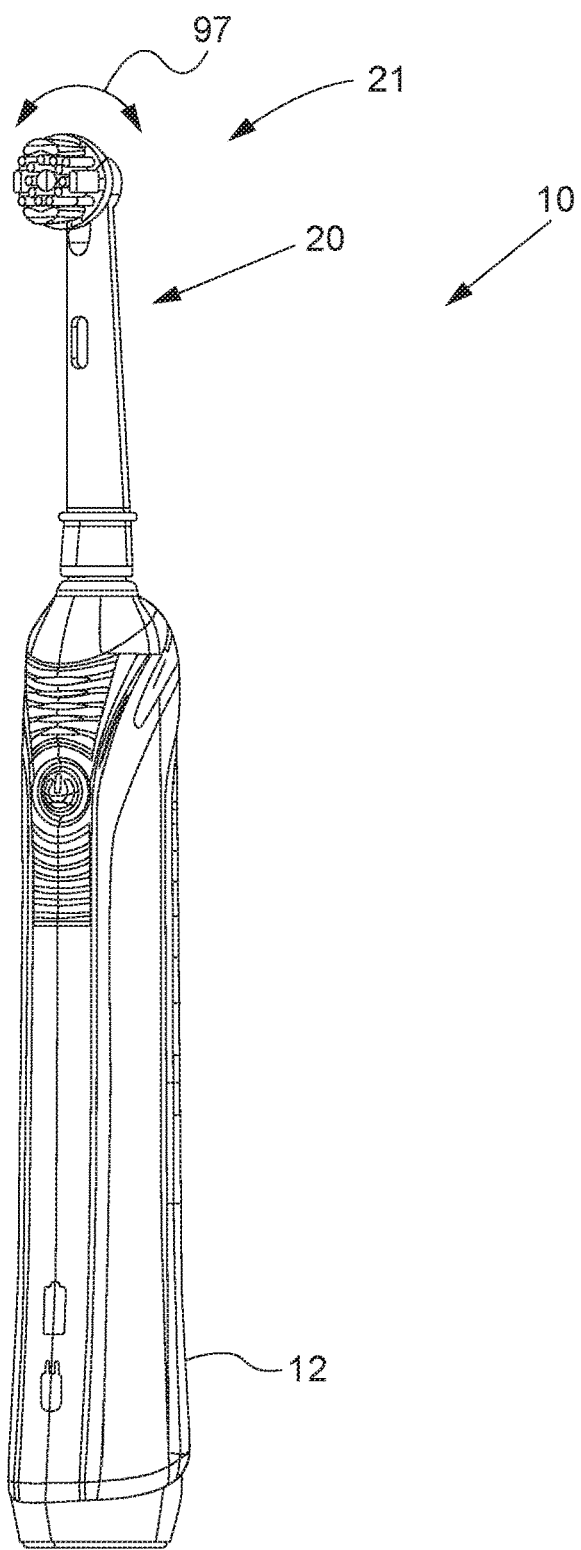
FIG. 1A is a perspective view showing a toothbrush constructed in accordance with an embodiment.
Figure 1B:
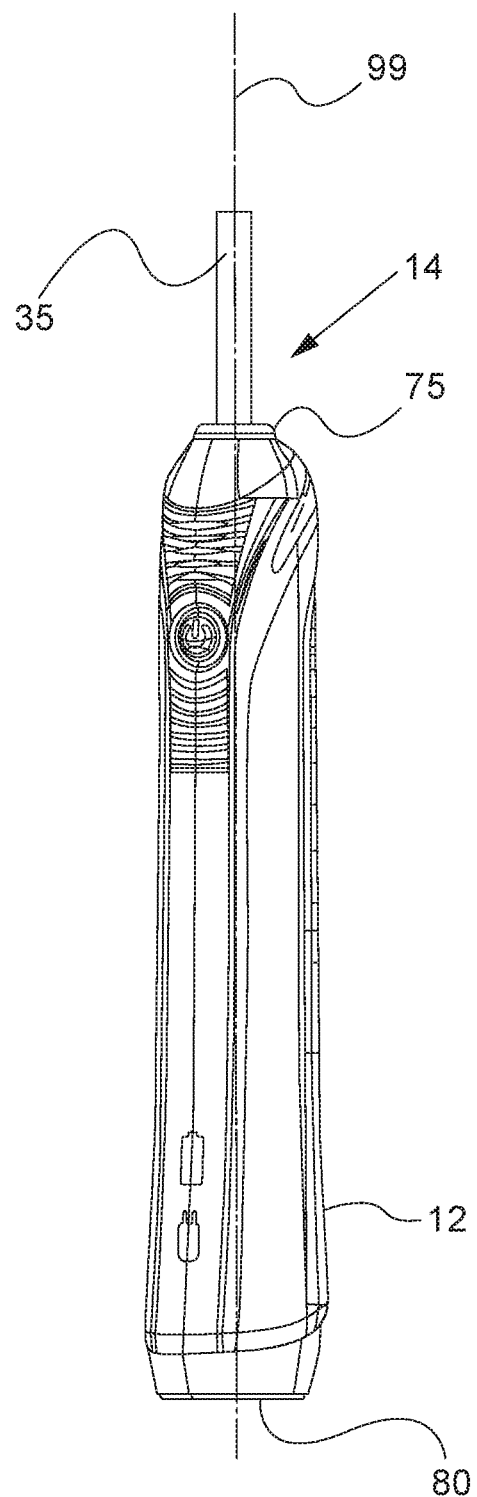
FIG. 1B is a perspective view showing a handle of the toothbrush of FIG. 1A.
Figure 1C:
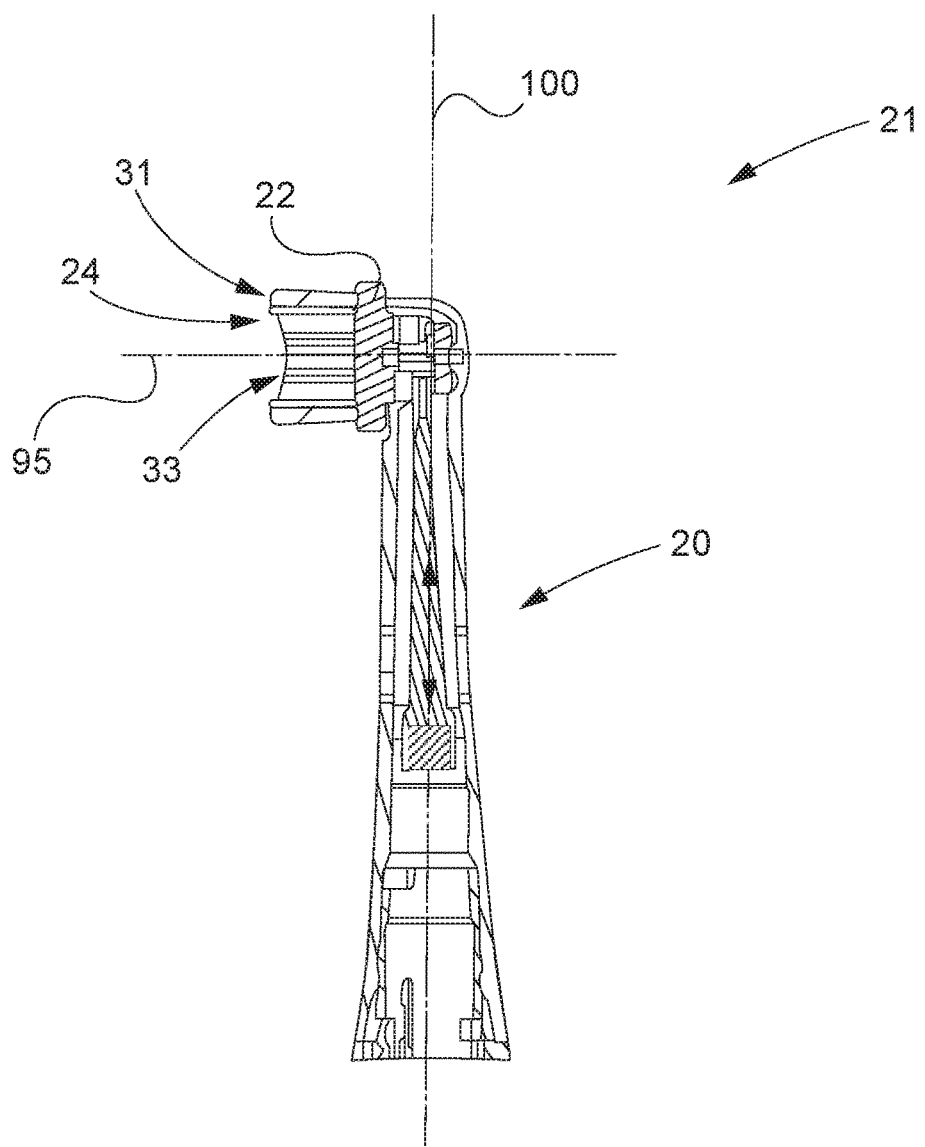
FIG. 1C is a cross section taken along a longitudinal axis showing a refill of the toothbrush of FIG. 1A.

Referring to FIGS. 1A and 1C, in one embodiment a toothbrush 10 comprises a handle 12 and a personal care attachment, e.g. refill 21. The refill 21 may be removably attached to the handle 12. The handle 12 comprises an engagement portion 14 at a distal end 75 of the handle. The handle further includes a proximal end 80, longitudinal axis 99, and a drive shaft 35.

The drive shaft 35, when in operation, may be driven in a direction which is substantially parallel to the longitudinal axis 99. Additionally, a drive system (discussed hereafter) within the handle 12 may comprise a linear motor. In some embodiments, the drive system may not comprise gearing between the linear motor and drive shaft. In some embodiments, discussed hereafter, a drive shaft may be provided with oscillating/rotating motion.

The refill 21 comprises a housing 20 and contact element carrier 22 that is rotatably coupled to the housing 20. A plurality of contact elements 24 are attached to the contact element carrier 22. The refill 21 comprises a longitudinal axis 100 which can, in some embodiments, be co-linear with the longitudinal axis 99 of the handle 12 when the housing 20 engages the engagement portion 14. The contact element carrier 22 oscillates about a rotational axis 95 such that the contact element carrier 22 rotates back and forth as shown by double arrow 97.

Figure 2:
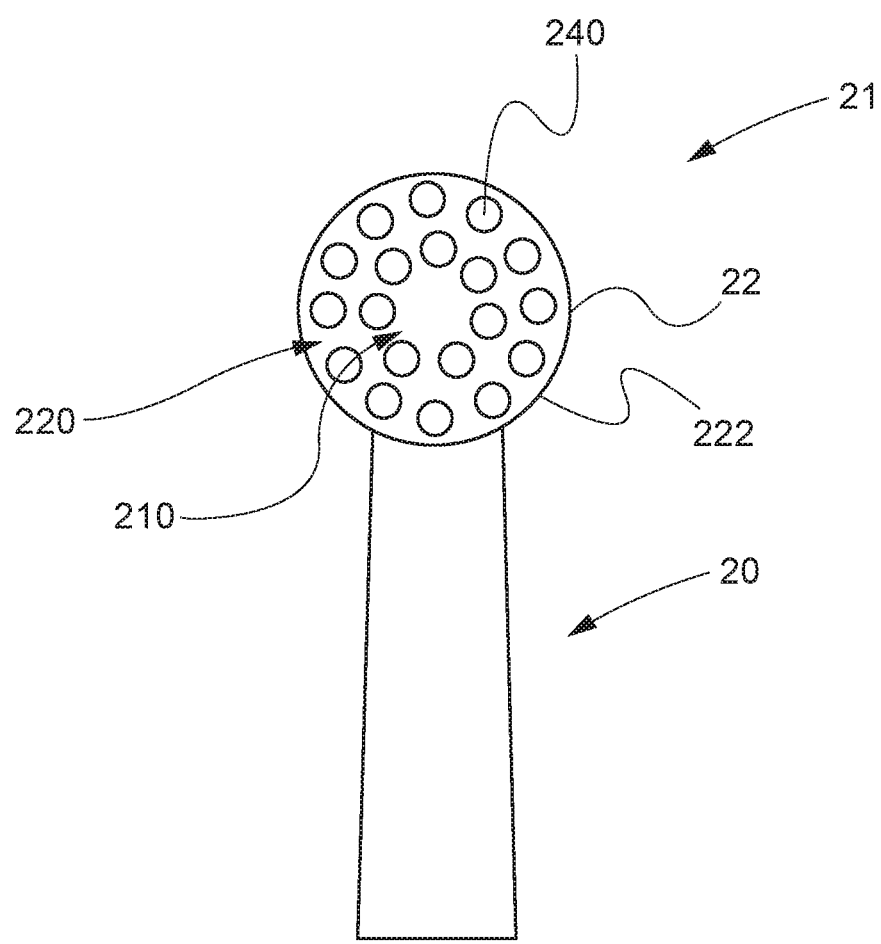
FIG. 2 is a close up view showing a front face of a contact carrier element of the refill of FIG. 1C.

As shown in FIG. 2, the contact element carrier 22 comprises an inner region 210 and a peripheral region 220. The peripheral region 220 is disposed adjacent a periphery 222 of the contact element carrier 22. The inner region 210 is disposed inboard of the peripheral region 220, i.e. nearer the rotational axis 95 (shown in FIG. 1C).

The contact elements 24 may be disposed in openings 240 in the contact element carrier 22. The portion of the contact element 24 disposed in the opening 240 is the attached end. The contact elements 24 extend to a tip end opposite the attached end. The contact elements 24 may be attached to the cleaning element carrier 22 by any suitable means. For example, stapling or anchoring may be utilized. As yet another example, the contact elements 24 may be attached to the contact element carrier 22 via anchorless technologies, e.g. in mold tufting (IMT), anchor free tufting (AFT), the like, or combinations thereof Additionally, embodiments are contemplated where combinations of anchor free and anchor tufting may be utilized. Additional attachment methods may be available depending on the type of contact element utilized. Such additional attachment methods are discussed hereafter.

Referring to FIGS. 1C and 2, the contact elements 24 comprise a first plurality of contact elements 33 arranged on the contact element carrier 22 in the inner region 210, and a second plurality of contact elements 31 arranged on the contact element carrier 22 in the outer region 220.

As stated previously, the contact elements 24 comprise an attached end and a tip end. In some embodiments, the tip ends of the second plurality of contact elements 31 are driven such that at least a portion of, if not all of the second plurality of contact elements 31 have a tip speed of about 1.5 m/s or greater. It is believed that with tip speeds of about 1.5 m/s or greater, liquid flows in the oral cavity may be generated which contribute to the cleaning of oral surfaces.

Figure 3:
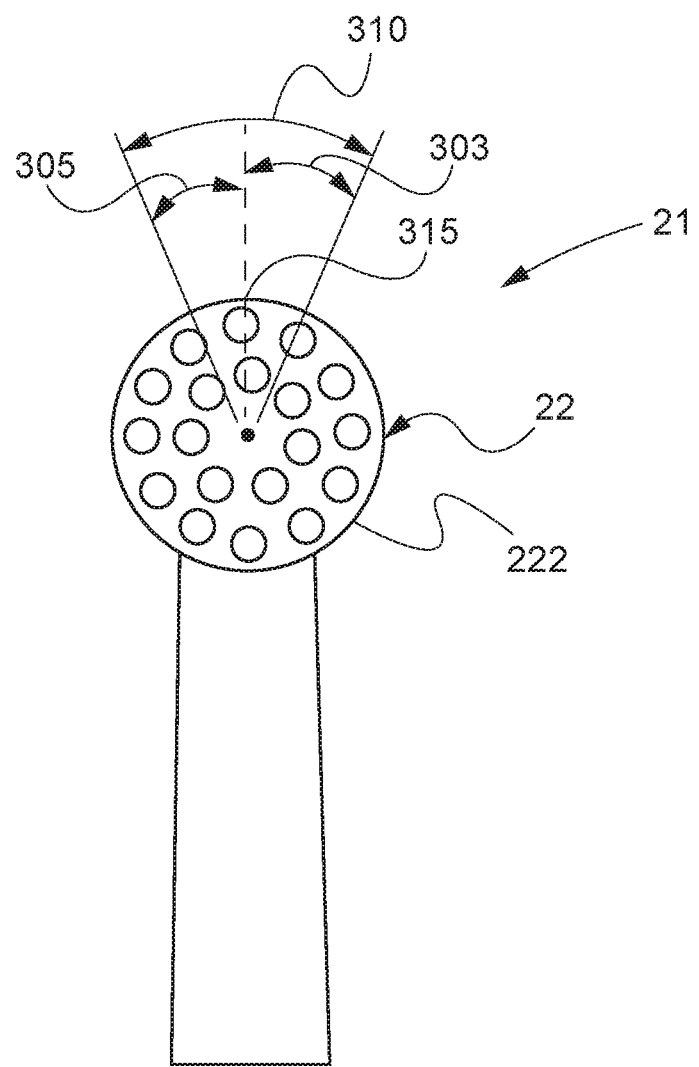
FIG. 3 is a close up view showing the front face of the contact carrier element of the refill of FIG. 1C and an oscillation displacement angle.

The tip speeds of the contact elements 24 are determined by the following equation:

$$V = 2\pi f A$$

where f=frequency of oscillation and A=amplitude. The amplitude is calculated based, in part, upon an oscillation displacement angle. As shown in FIGS. 2 and 3, the oscillation displacement angle 310 is defined by the movement of point 315 on the periphery 222 of the contact element carrier 22. With respect to the rotational axis 95 (shown in FIG. 1C) point 315 may rotate in a first direction at a first angle 305 and in a second direction at a second angle 303 during operation. The first angle 305 and the second angle 303 cumulatively form the displacement angle 310. The amplitude is then determined by the following equation:

$$A = \frac{\alpha \pi r}{180}$$

where α=the displacement angle 310 and r is the distance from the rotational axis 95 (shown in FIG. 1C) to a center point of the opening 240 (shown in FIG. 2) in which the contact element for which the tip speed is being determined is disposed. It is worth noting that in some embodiments, the radius of the contact element carrier is usually measured in millimeters where the velocity (tip speed) being determined is in meters. So, some additional calculations may be required to convert the units for the amplitude and/or the velocity to ensure that m/s is derived in the tip speed equation.

Additionally, because amplitude is based, in part, upon the radius that the contact element is away from the rotational axis 95 (shown in FIG. 1C), the first plurality of contact elements 33 should have lower tip speeds than those of the second plurality of contact elements 31. In some embodiments, the first plurality of contact elements 33 or a portion thereof are driven such that they have a tip speed of at least 1.5 m/s.

Generally, manufacturers try to utilize as much surface area of the contact element carrier as possible. As such, for larger diameter contact element carriers, a larger radius between the rotational axis and the outermost contact elements may be realized which can facilitate reaching the goal of 1.5 m/s at lower frequencies. However, the diameter of contact element carriers is constrained because of mouth feel, e.g. user perception. In general, larger diameter contact element carriers may be perceived as uncomfortable or too large to provide cleaning to an adequate number of teeth particularly those in the back of the oral cavity. For example, a contact element carrier having a large diameter, e.g. above 14 mm, may cause some discomfort to the user or seem bulky during use.

As such, the diameter of the contact element carrier 22, in some embodiments, is between about 8 mm to about 16 mm. The diameter of the contact element carrier 22 may be greater than about 8 mm, greater than about 9 mm, greater than about 10 mm, greater than about 11 mm, greater than about 12 mm, greater than about 13 mm, greater than about 14 mm, greater than about 15 mm, greater than about 16 mm, greater, or less than about 16 mm, less than about 15 mm, less than or equal to about 14 mm, less than about 13 mm, less than about 12 mm, less than about 11 mm, less than about 10 mm, or any number or any ranges including or within the values provided.

Figure 4:
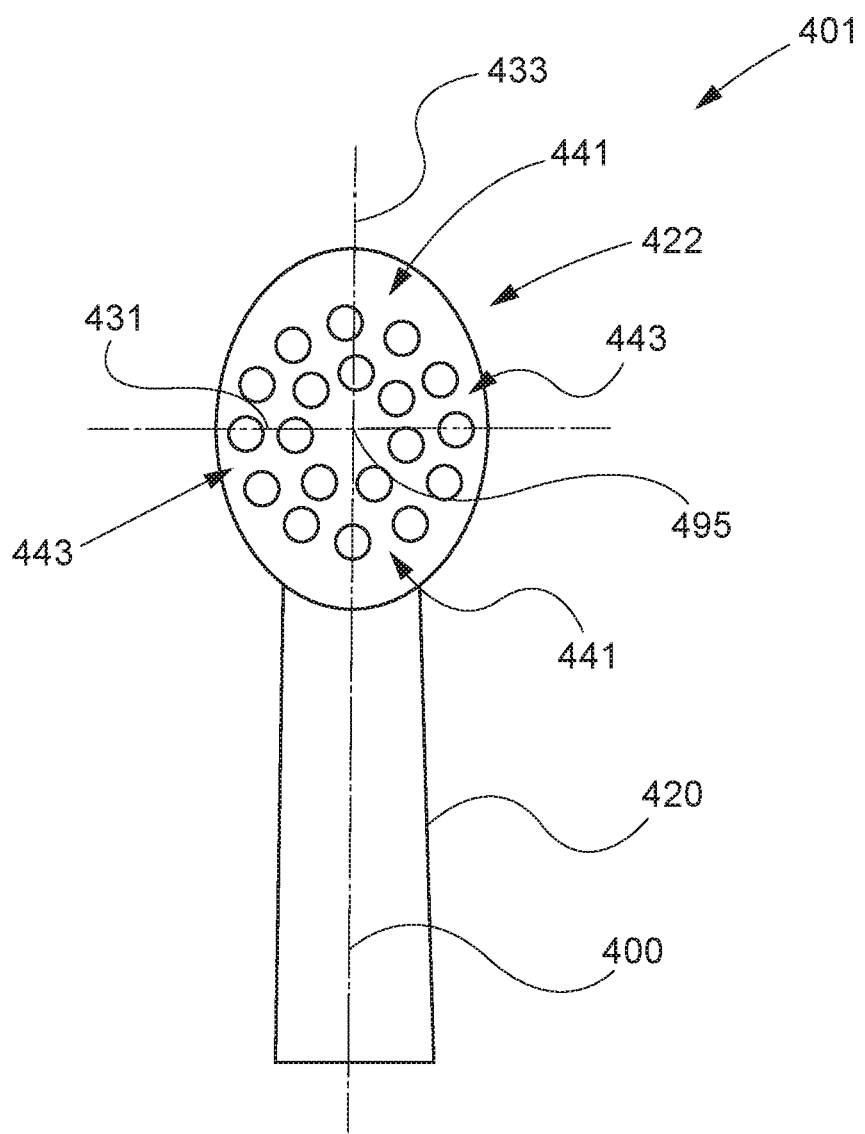
FIG. 4 is a close up view showing a front face of a contact carrier element another embodiment of a refill.

Referring to FIG. 4, in order to achieve greater coverage, i.e. contact element area, embodiments are contemplated where a contact element carrier 422 comprises a non-circular surface. For example, the contact element carrier 422 may comprise an oval or elliptical shape having a major axis 433 and a minor axis 431. As shown, the major axis 433 may be generally aligned with a longitudinal axis 400 of refill 401, in some embodiments. However, in some embodiments, the major axis 433 may be offset from the longitudinal axis 400 of the refill 401.

In some embodiments, a diameter along the minor axis 431 is between about 8 mm to about 16 mm as described above with regard to the diameter of the contact element carrier 22 and may be any number or range described heretofore with regard to the cleaning element carrier 22 (shown in FIG. 3). In some embodiments, a diameter along the major axis 433 is between about 9 mm to about 19 mm.

The major axis 433 may be greater than about 9 mm, greater than about 10 mm, greater than about 11 mm, greater than about 12 mm, greater than about 13 mm, greater than about 14 mm, greater than about 15 mm, greater than about 16 mm, greater than about 17 mm, greater than about 18 mm, greater than about 19 mm, or less than or equal to about 19 mm, less than about 18 mm, less than about 17 mm, less than about 16 mm, less than about 15 mm, less than about 14 mm, less than about 13 mm, less than about 12 mm, less than about 11 mm, less than about 10 mm, or any number within or any range within or including the values above. In such embodiments, the radius is measured in the same way as described heretofore, i.e. distance from a rotational axis 495 to a center point of the contact element or to the center point of the opening in in which the desired contact element resides. The equations provided above may be applied to contact element carriers having an oval or elliptical surface.

For those embodiments where the contact element carrier 422 comprises an oval or elliptical shape, a second plurality of contact elements 441 may be disposed on opposite sides of the contact element carrier 422 adjacent the major axis 433. In some embodiments, the contact element carrier 422 is driven at a frequency and/or amplitude such that the second plurality of contact elements 441 have a tip speed of at least 1.5 m/s. Additionally, in some embodiments, the contact element carrier 422 is driven at a frequency and/or amplitude such that a first plurality of contact elements 443 adjacent the minor axis 431 have a tip speed of at least 1.5 m/s. In other embodiments, the contact element carrier 422 may be driven at a frequency and/or amplitude such that the second plurality of contact elements 441 have a tip speed of at least 1.5 m/s while the first plurality of contact elements 443 have a tip speed of less than 1.5 m/s.

Many tip speeds may be utilized for the contact elements. For example, the second plurality of contact elements may have a tip speed of at least 2.5 m/s. In some embodiments, the tip speed of a portion of the contact elements may be greater than about 1.3 m/s, greater than about 1.4 m/s, greater than about 1.5 m/s, greater than about 1.6 m/s, greater than about 1.7 m/s, greater than about 1.8 m/s, greater than about 1.9 m/s, greater than about 2.0 m/s, greater than about 2.1 m/s, greater than about 2.2 m/s, greater than about 2.3 m/s, greater than about 2.4 m/s, greater than about 2.5 m/s, or less than about 2.5 m/s, less than about 2.4 m/s less than about 2.3 m/s, less than about 2.2 m/s, less than about 2.1 m/s, less than about 2.0 m/s, less than about 1.9 m/s, less than about 1.8 m/s, less than about 1.7 m/s, less than about 1.6 m/s, less than about 1.5 m/s, or any number or any range within or including these values.

As shown in the above equations, a tip speed of 1.5 m/s can be achieved via a larger radius, i.e. distance from the rotational axis to the contact element for which the velocity is being determined. However, as discussed previously, the size of the contact element carrier may be constrained because of mouth feel during use. Additionally, the tip speed of 1.5 m/s can be achieved via the amplitude of the contact element carrier 22, 422. However, as above, the amplitude may be constrained by a user based upon mouth feel. For example, a large oscillation displacement angle, which impacts amplitude, can cause the user to feel that the brush is too aggressive. In contrast, too low of an oscillation displacement angle can cause inhibit the cleaning effect of the toothbrush, but also may impact the frequency of operation such that too high of an operating frequency is required to achieve a 1.5 m/s tip speed.

Additionally, a larger amplitude may be difficult to achieve because of cost considerations. For example, for larger amplitudes ball bearings or springs may be required which can increase the cost and complexity of the refill.

In some embodiments, the oscillation displacement angle 310 (shown in FIG. 3) is greater than about 5 degrees to about 60 degrees. The oscillation displacement angle 310 (shown in FIG. 3) may be greater than about 5 degrees, greater than about 10 degrees, greater than about 15 degrees, greater than about 20 degrees, greater than about 25 degrees, greater than about 30 degrees, greater than about 35 degrees, greater than about 40 degrees, greater than about 45 degrees, greater than about 50 degrees, greater than about 55 degrees, greater than about 60 degrees, or less than about 60 degrees, less than about 55 degrees, less than about 50 degrees, less than about 45 degrees, less than about 40 degrees, less than about 35 degrees, less than about 30 degrees, less than about 25 degrees, less than about 20 degrees, less than about 15 degrees, less than about 10 degrees, or any number or any range within or including the values provided.

Also as shown by the previous equations, the frequency of operation also impacts tip speed. Similar constraints may be present with regard to operating frequency. For example, an operating frequency which is too low may make a user feel like the device is not operating properly or not performing as well as it should. In contrast, too high of an operating frequency may cause the user to feel that the device is too aggressive. Additionally, to high of an operating frequency may produce higher noise levels which can irritate the user. These higher noise levels may be particularly relevant where the drive frequency and the resonance frequency of the personal care device or the resonance of the personal care attachment, e.g. refill 21, 401, are close together. The discussion of resonance frequency and noise levels is provided hereafter.

In contrast, in some embodiments, the toothbrushes may utilize a desired operating frequency and/or a desired oscillation displacement angle in order to achieve a tip speed of at least 1.5 m/s, while also emitting/producing reduced noise levels during operation. The noise levels of the toothbrushes constructed in accordance with the invention are discussed hereafter.

Additionally, a user's perception of a specific movement can be varied depending on the frequency of the movement. For example, a specific movement at a frequency below 120 Hz may be very perceptible to a user whereas the same movement at a frequency of greater than about 120 Hz is less perceptible. In some embodiments, the operating frequency is greater than about 120 Hz. The operating frequency can be greater than about 120 Hz, greater than about 130 Hz, greater than about 140 Hz, greater than about 150 Hz, greater than about 160 Hz, greater than about 170 Hz, greater than about 180 Hz, greater than about 190 Hz, greater than about 200 Hz, or less than about 200 Hz, less than about 190 Hz, less than about 180 Hz, less than about 170 Hz, less than about 160 Hz, less than about 150 Hz, less than about 140 Hz, less than about 130 Hz, and/or any number or any range within or including these values.

Conventional brushes often can provide operating frequencies of less than 100 Hz and/or oscillation displacement angles of about 20 degrees in no load conditions; however, in the loaded state, often times oscillation displacement angle and/or frequency can drop significantly. With some conventional toothbrushes, an applied load to the contact element field causes a decrease in the frequency; however, due to the gearing in the handle and/or refill, the oscillation displacement angle remains constant.

Motor Control

Because the cleaning fluid flows described above occur within the oral cavity when contact elements have tip speeds of at least 1.5 m/s, in some embodiments, the amplitude and/or frequency may be kept at a desired level in both load and no load conditions in order to achieve the 1.5 m/s tip speed for at least a portion of the contact elements. For example, in some embodiments, the toothbrushes may comprise a load detector which can determine the load applied to the toothbrush during brushing. The load detector can be in signal communication with a controller.

In some embodiments, a toothbrush may comprise a detector which measures an operating parameter of a motor and detects changes therein. The operating parameter may comprise at least one of speed, amplitude, operating frequency, the like, or combinations thereof. Additionally, in some embodiments, a characteristic electrical parameter may be measured in addition to or indepently of the operating parameters mentioned previously. In such embodiments, the characteristic electrical parameters may include current consumption. Additional embodiments are contemplated where load is determined based upon input from the motor. Such embodiments are discussed in the following patent applications Serial Numbers EP11006100.9 and EP11006064.7.

Regardless of how loaded versus an unloaded state are determined for the toothbrush, when in a loaded state, i.e. during brushing, the controller may adjust the pulse width modulation (PWM) of the power supplied to a motor in an effort to keep the oscillation displacement at a desired level such that the tip speed of at least 1.5 m/s is achieved on at least a portion of the contact elements. For example, in order to modify the oscillation displacement angle, the width of the pulses provided to the motor may be increased thereby supplying more power per pulse. As such, an increase in the pulse width may result in greater oscillation displacement angle. In order to modify the frequency, the centerline spacing between pulses can be varied. For example, increased centerline spacing between pulses results in a lower frequency while decreased centerline spacing between pulses results in increased frequency. Adjustment of the PWM will be considered to include the modification of width of an individual pulse or a plurality of pulses and/or modification to the centerline spacing between adjacent pulses. For the personal care devices of the embodiments described, an applied load only impacts amplitude and not frequency.

As stated previously, in at least one operational mode, a contact element carrier may be driven such that a plurality of contact elements have a tip speed of at least 1.5 m/s. A desired range of frequencies (discussed heretofore as the operating frequency) and/or desired range of oscillation displacement angles (discussed heretofore as oscillation displacement angle) may be utilized to accomplish this tip speed. In some embodiments, the toothbrushes can maintain an operating frequency within the desired range of frequencies and/or an operating oscillation displacement angle within the desired range of oscillation displacement angles even with loads of greater than zero newtons, e.g. about 2 N to about 3 N, applied to the contact element field. For example, when a load above zero N is detected, the PWM may be modified such that the drive system maintains an oscillation displacement angle which is within the desired oscillation displacement angle range. As another example, under no load, a first operating oscillation displacement angle may be realized. Under a load of about greater than zero newtons to about 3 N, a second operating oscillation displacement angle may be realized, where the second operating oscillation displacement angle is at least about 74 percent of the first operating oscillation displacement angle. In some embodiments, the contact element carrier may have a second operating oscillation displacement angle which is at least about 74 percent of the first oscillation displacement angle, at least about 75 percent, at least about 80 percent, at least about 85 percent, at least about 90 percent, at least about 95 percent, at least about 98 percent, at least about 99 percent, at least about 100 percent, and/or any number or any ranges within or including the values above.

Oscillation displacement angles impact the amplitude. As such, the oscillation displacement angle under no load may be about 40 degrees and the oscillation displacement angle under load is about 30 degrees. In some embodiments, under a load of about 1 N to about 3N, the oscillation displacement angle may be about 10 degrees. Oscillation displacement angles under no load and under load are shown in FIG. 5 for prototypes of toothbrushes constructed in accordance with the present invention.

Figure 5:
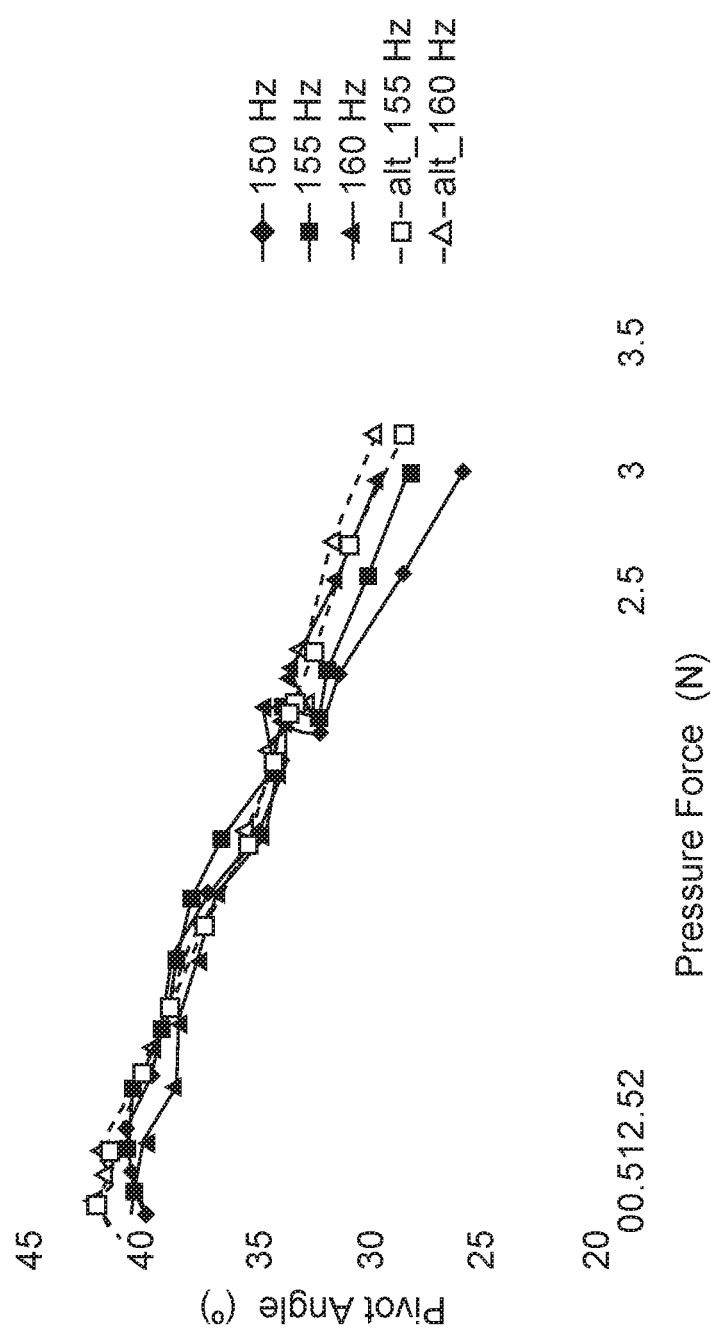
FIG. 5 is a graph showing the oscillation displacement angle for a plurality of refills under varying loads and under no load.

As shown in FIG. 5, some prototypes were tested under no load and under various applied loads. Some of the prototypes were tested at multiple frequencies. For each of the prototypes tested, at no load, the oscillation displacement angle was about 40 degrees. Under a 1 N load, the oscillation displacement angle for each prototype dropped to slightly below 40. Even at a loading of about 3 N, the prototypes provided an oscillation displacement angle of between about 25 degrees and about 30 degrees. Accordingly, if at a load of 3 N, the tip speed of at least a portion of the contact elements is at least 1.5 m/s, then because of the higher oscillation displacement angles at a load of 1N, assuming the same operating frequency at 1 N and at 3 N, the tip speed of the at least a portion of contact elements would be greater than 1.5 m/s. In such instances, the PWM may be adjusted down for the lighter load such that either the oscillation displacement angle and/or the frequency are reduced such that the at least a portion of contact elements are have tip speeds of about 1.5 m/s.

Another problem with conventional toothbrushes is that generally when initially powered on, the toothbrush operates at full speed, e.g. maximum frequency and/or maximum amplitude. For example, a conventional toothbrush having an operating frequency under no load of 75 Hz and a displacement angle of 20 degrees under no load will generally operate at that frequency and displacement angle the instant that the toothbrush is turned on. However, this can be problematic in that if a user applies toothpaste to the contact element field, the frequency and displacement angle of the toothbrush will tend to fling the toothpaste off of the contact elements. Additionally, when a user is done brushing, the removal of the toothbrush from the oral cavity, in the powered on state, can cause similar problems, i.e. flinging of used toothpaste off of the contact element field.

As such, in some embodiments, toothbrushes may comprise a controller which provides an idle run state for a no load condition and a normal run state for a loaded condition, wherein the idle run state and the normal run state are different. For example, during the normal run state, i.e. during brushing, the controller may adjust the PWM such that the tip speed of the second plurality of contact elements is at least 1.5 m/s. In contrast, during the idle run state, e.g. outside of the oral cavity under no load, the controller may adjust the PWM such that the tip speed of the second plurality of contact elements is less than 1.5 m/s. In some embodiments, the adjustment of the PWM may impact the operating frequency and/or the oscillation displacement angle which impacts amplitude.

In such embodiments, the controller may be configured such that if a load of about zero newtons is detected, the idle run state, e.g. no load, is implemented. The idle run state may be selected automatically by the controller when the toothbrush is initially powered on. Additionally, after a brushing for a predetermined time period, e.g. two minutes, three minutes, the controller may initiate the idle run state such that the user removing the toothbrush from his/her mouth does not fling used toothpaste from the contact element field. Additionally, the initiation of the idle run state after the predetermined time can signal the user that he/she has brushed for a sufficient amount of time.

If a load above or equal to about zero newtons is detected, then a normal run state may be implemented. In the normal run state, the controller may adjust the PWM to ensure that the second plurality of contact elements have a tip speed of at least 1.5 m/s. If a load of about 3 N is detected, then a third run state may be implemented. In the third run state, the controller may again, adjust the PWM thereby increasing the power supplied to the drive system. The adjustment of the PWM in the third run state would be to ensure that the second plurality of contact elements maintain a tip speed of at least 1.5 m/s even under an increased load.

In some embodiments, if a load above or equal to about 3 N is detected, then the PWM may be adjusted such that damage to the teeth and/or gums of a user is reduced or precluded altogether. For example, for an exerted force that could cause harm to the teeth and/or gums to the user, the controller may adjust the PWM such that the amplitude and/or frequency are reduced.

In the idle run state under no load and/or in the after brushing state described above, the PWM may be adjusted such that the amplitude is reduced from that of the norlam run state. For example, the amplitude may be reduced be less than or equal to about 30 percent, less than about 25 percent, less than about 20 percent, less than about 15 percent, less than about 10 percent, or any number or any range within or including the values provided.

Similarly, in the idle run state under no load and/or in the after brushing state described above, the PWM may be adjusted such that there is a decrease in frequency from that of the normal run state. For example, the frequency may be reduced by less than or equal to about 30 percent, less than about 25 percent, less than about 20 percent, less than about 15 percent, less than about 10 percent, or any number or any range within or including the values provided.

In some embodiments, the toothbrushes can offer the user with a large amount of flexibility. In addition to the idle run state and the normal run state, many other additional operating options may exist. For example, as stated previously, adjustment of the PWM can impact the amplitude as well as the frequency. As such, a controller, in some embodiments, can provide the user with a plurality of operating modes which modify either the amplitude and/or the frequency. In contrast, conventional toothbrushes have gearing within the handle and/or the refill which fixes the oscillation displacement angle regardless of the voltage applied to the motor. As such, adjustments to the PWM of a conventional toothbrush results only in changes to the operating frequency.

With regard to the variation in amplitude, any increase or decrease may be realized by modifying the oscillation displacement angle. As such hereafter, an increase in amplitude can mean an increase in oscillation displacement angle while a decrease in amplitude can mean a decrease in oscillation displacement angle.

In some embodiments, a controller may allow the user to select an operation mode in which the amplitude is increased by up to about 25% for a predetermined period of time. For convenience, the AI (amplitude increase) mode. The increase in amplitude may be any suitable percentage of the desired amplitude (discussed heretofore). For example, the increase in amplitude may be greater than about 5 percent, greater than about 10 percent, greater than about 15 percent, greater than about 20 percent, greater than about 25 percent, or less than or equal to about 25 percent, less than about 20 percent, less than about 15 percent, less than about 10 percent, less than about 5 percent, or any number within or any range within or including these values.

The predetermined period of time may be any suitable time period. For example, the increase in amplitude may occur for between about 1 second to about 30 seconds. The predetermined period of time may be greater than about 1 second, greater than about 5 seconds, greater than about 10 second, greater than about 15 seconds, greater than about 20 seconds, greater than about 25 seconds, or less than or equal to about 30 seconds, less than about 25 seconds, less than about 20 seconds, less than about 15 seconds, less than about 10 seconds, less than about 5 seconds, or any number within or any range including or within the values provided. Embodiments are contemplated where the amplitude boost occurs more than once during a single brushing routine.

The AI mode may be beneficial where at least some of the contact elements comprise elastomeric elements which can provide gum massaging as well as polishing functions. With a larger amplitude, e.g. oscillation displacement angle, the elastomeric elements may provide both functions, in some embodiments.

Additionally, embodiments are contemplated where the user selects the AI mode via a push button on the handle. For example, if the user is aware of a problematic tooth from a cleaning standpoint, the user may depress the pushbutton in order to increase the amplitude for a predetermined period of time.

In some embodiments, the controller may allow the user to select an operation mode where at least a portion of the contact elements have tip speeds of at least 1.5 m/s. For convenience, the TS (tip speed) mode, e.g. normal mode. Embodiments are contemplated where a handle may recognize the refill attached thereto and adjust the PWM as required in order to achieve the tip speed of 1.5 m/s in at least a portion of the contact element field. For example, for a first refill, the controller may adjust the PWM to a first level to achieve the 1.5 m/s in at least a portion of the contact elements. For a second refill, the controller may adjust the PWM to a second level to achieve the 1.5 m/s in at least a portion of the contact elements, wherein the first level and the second level are different. So, if the first refill has a larger radius than the second refill, either amplitude and/or frequency may be lower than the frequency and/or amplitude utilized for the second refill. Additionally, where the refill is recognized by the handle and/or the display, the PWM may be adjusted based upon the type of contact elements present on the refill. For example, for a first refill comprising only bristle tufts, the at least 1.5 m/s may be achieved by increasing the amplitude and/or frequency. In contrast, for a second refill having elastomeric elements suitable for polishing the at least 1.5 m/s may be achieved by increasing the increasing the frequency and decreasing the amplitude (see the FI/AD mode discussed hereafter). Such communication between the handle, the refill, and/or a display are disclosed in U.S. Pat. Nos. 7,086,111; 7,673,360; and 7,024,717; and in U.S. Patent Application Publication Nos. 2008/0109973A1; 2010/0170052A1; and 2010/0281636A1.

In some embodiments, the controller may allow an operation mode to be selected by the user which is for the purpose of performing a soft or sensitive operation. For convenience, the AD (amplitude decrease) mode. The AD mode may comprise a reduction in amplitude from desired amplitude from between about 5 percent to about 50 percent. Any suitable reduction may be utilized. For example, the reduction in the amplitude may be greater than about 5 percent, greater than about 10 percent, greater than about 15 percent, greater than about 20 percent, greater than about 25 percent, greater than about 30 percent, greater than about 35 percent, greater than about 40 percent, greater than about 45 percent, or less than or equal to about 50 percent, less than about 45 percent, less than about 40 percent, less than about 35 percent, less than about 30 percent, less than about 25 percent, less than about 20 percent, less than about 15 percent, less than about 10 percent, or any number within or any range including or within the values provided. In the AD mode, the controller may increase the frequency above that of the desired frequency (discussed heretofore) such that the 1.5 m/s tip speed is maintained by at least a portion of the contact elements, in some embodiments. In other embodiments, the AD mode may maintain the operational frequency from desired frequency and simply reduce the amplitude as discussed above.

In some embodiments, the controller may allow the user to choose an operation mode which is a gum care mode. For convenience, the AV (amplitude variation) mode. The AV mode may comprise a variation of the amplitude which occurs at predetermined time intervals. The variation of the amplitude can be between greater than about 25 percent of the desired amplitude to about a reduction of about 50 percent of desired amplitude. Any suitable variation in amplitude may be utilized. For example, the variation for the increase in amplitude may be greater than about 5 percent, greater than about 10 percent, greater than about 15 percent, greater than about 20 percent, or less than or equal to about 25 percent, less than about 20 percent, less than about 15 percent, less than about 10 percent, less than about 5 percent, or any number within or any range within or including the values provided. With regard to the decrease in amplitude, the variation may be greater than about 5 percent, greater than about 10 percent, greater than about 15 percent, greater than about 20 percent, greater than about 25 percent, greater than about 30 percent, greater than about 35 percent, greater than about 40 percent, greater than about 45 percent, or less than or equal to about 50 percent, less than about 45 percent, less than about 40 percent, less than about 35 percent, less than about 30 percent, less than about 25 percent, less than about 20 percent, less than about 15 percent, less than about 10 percent, or any number within or any range within or including the values provided.

As stated previously, the variation in the amplitude can occur at predetermined intervals. Any suitable time period may be selected. For example, the variation may occur greater than about every 1 second, greater than about every 5 seconds, greater than about every 10 second, greater than about every 15 seconds, greater than about every 20 seconds, greater than about every 30 seconds, or any number or range within or including these values.

The variation of the amplitude may occur at any suitable time during the brushing routine. For example, the amplitude variation may occur prior to the normal brushing routine by the user. As another example, the variation can occur after the brushing routine of the user. As another example, the variation may occur during the brushing routine of the user.

The variations in amplitude may alternate between an increase in the amplitude above the desired amplitude followed by a decrease in amplitude below the desired amplitude. For example, in a first cycle, the amplitude may be increased by about 20 percent above a desired amplitude, and in a second cycle the amplitude may decrease by about 30 percent below the desired amplitude. In some embodiments, the increase in amplitude above the desired level may be the same as the value of decrease below of the desired level. For example, in a first cycle, the amplitude may be increase by about 20 percent above the desired amplitude, and in a second cycle the amplitude may be decrease by about 20 percent below the desired amplitude.

The variation of the amplitude may have any suitable time duration. For example, when the amplitude is either increased or decreased from the desired amplitude, the change in amplitude may last for a time period of greater than about 1 second, greater than about 5 seconds, greater than about 10 seconds, greater than about 20 seconds, greater than about 25 seconds, greater than about 30 seconds, greater than about 35 seconds, greater than about 40 second, greater than about 45 seconds, greater than about 50 second, greater than about 55 second, greater than about 60 second, or less than about 60 second, less than about 55 seconds, less than about 50 seconds, less than about 45 seconds, or less than or equal to about 40 seconds, less than about 35 seconds, less than about 30 seconds, less than about 25 seconds, less than about 20 seconds, less than about 15 seconds, less than about 10 seconds, less than about 5 seconds, or any number within or any range within or including the values provided.

In some embodiments, the time duration of the variation may depend upon whether the variation is an increase or a decrease in the desired amplitude. For example, in some embodiments, an increase in amplitude above the desired amplitude may have a first time duration while a decrease in amplitude below the desired amplitude may have a second time duration. In some embodiments, the first time duration may be the same as the second time duration. In some embodiments, the first time duration may be different than the second time duration. For example, the first time duration may be longer than the second time duration. As yet another example, the second time duration may be longer than the first time duration.

In some embodiments, the increases and/or decreases may be arranged in any suitable manner. For example, in some embodiment, a first increase may occur at a first predetermined time period and last a first time duration. After the first time duration, the amplitude may return to the desired level for a predetermined time period. Subsequently, a second increase may occur at a second predetermined time and last for a second time duration. After the second time duration, the amplitude may again return to the desired level or may decrease. The subsequent adjustment of the amplitude may be another increase or a decrease from the desired amplitude. Similarly, any decreases in amplitude from the desired amplitude may occur as described above with regard to the first increase and the second increase.

Any number of combinations may be created. For example, an increase followed by a decrease, an increase followed by an increase, a decrease followed by an increase, or a decrease followed by a decrease. Additionally, between any of the increases or decreases, the amplitude may return to the desired amplitude.

In some embodiments, the controller may allow the user to select a mode of operation which comprises a change in both frequency and amplitude. For convenience, the FV/AV (frequency variation/amplitude variation) mode. The change in frequency can be any suitable increase or decrease. For example, in some embodiments, the frequency may increase above the desired frequency by greater than about 5 Hz, greater than about 10 Hz, greater than about 15 Hz, greater than about 20 Hz, greater than about 25 Hz, greater than about 30 Hz, or less than or equal to about 30 Hz, less than about 25 Hz, less than about 20 Hz, less than about 15 Hz, less than about 10 Hz, less than about 5 Hz, or any numbers within or any ranges within or including the values provided.

Similarly, the change in frequency may be a decrease from the desired frequency. For example, in some embodiments, the frequency may decrease by greater than about 5 Hz, greater than about 10 Hz, greater than about 15 Hz, greater than about 20 Hz, greater than about 25 Hz, greater than about 30 Hz, or less than or equal to about 30 Hz, less than about 25 Hz, less than about 20 Hz, less than about 15 Hz, less than about 10 Hz, less than about 5 Hz, or any numbers within or any ranges within or including the values provided.

Also, the amplitude may be any suitable increase or decrease. For example, in some embodiments, the amplitude may increase or decrease with regard to the desired amplitude as described heretofore with regard to the AV mode. Similarly, the time periods of variation as well as the time periods for the duration of these changes to frequency and/or amplitude may be as described with regard to the AV mode. Additionally, an increase in frequency may be accompanied by an increase in amplitude in some embodiments. In other embodiments, an increase in frequency may be accompanied by a decrease in amplitude. In other embodiments, an increase in amplitude may be accompanied by a decrease in frequency. And, in other embodiments, a decrease in amplitude may be accompanied by a decrease in frequency.

In some embodiments, the controller may allow the user to select a mode of operation which may be suitable for tongue cleaning. For convenience, FI/AD2 (frequency increase/amplitude decrease) mode. The increase in frequency above that of the desired frequency may be as described with regard to the FV/AV mode. The AD2 portion of the FI/AD2 mode may comprise any suitable reduction in amplitude from the desired range of amplitudes. The FI/AD2 mode may comprise a reduction in amplitude from desired amplitude from between about 5 percent to about 75 percent. For example, the reduction in the amplitude may be greater than about 5 percent, greater than about 10 percent, greater than about 15 percent, greater than about 20 percent, greater than about 25 percent, greater than about 30 percent, greater than about 35 percent, greater than about 40 percent, greater than about 45 percent, greater than about 50 percent, greater than about 55 percent, greater than about 60 percent, greater than about 65 percent, greater than about 70 percent, or less than or equal to about 75 percent, less than about 70 percent, less than about 65 percent, less than about 60 percent, less than about 55 percent, less than about 50 percent, less than about 45 percent, less than about 40 percent, less than about 35 percent, less than about 30 percent, less than about 25 percent, less than about 20 percent, less than about 15 percent, less than about 10 percent, or any number or range including or within these values.

Because tongue cleaning may occur after the course of a brushing routine, the FI/AD2 mode may begin automatically after a predetermined amount of time, i.e. after the brushing routine. For example, the FI/AD2 mode may begin after about two minutes or after about three minutes, or any number or any range within or including these values.

In some embodiments, the controller may allow the user to select a mode of operation which may be suitable for polishing teeth. For convenience, HF/AD, (high frequency/amplitude decrease) mode. The increase in frequency may be any suitable increase. For example, the frequency may increase by greater than about 25 percent over that of the desired frequency, greater than about 30 percent, greater than about 35 percent, greater than about 40 percent, greater than about 45 percent, greater than about 50 percent, greater than about 60 percent, greater than about 70 percent, greater than about 80 percent, greater than about 90 percent, greater than about 100 percent, or less than about 100 percent less than about 90 percent, less than about 80 percent, less than about 70 percent, less than about 60 percent, less than about 50 percent, less than about 40 percent, less than about 30 percent, or any number or range within or including these values. The decrease in amplitude from that of the desired amplitude may be as described heretofore with regard to the AD mode.

In some embodiments, the controller may allow the user to select a mode of operation which provides a massage function. For convenience, the FV (frequency variation) mode. The variation in frequency may be any suitable amount. Some examples of the variation in frequency are provided with regard to the FV/AV mode.

Embodiments are contemplated where the personal hygiene system of comprises storage (memory) capability. For example, a user may have a saved profile in which the amplitude is slowly increased during brushing. And, at the conclusion of the brushing session, e.g. two minutes, the frequency may be increased to perform a polishing and/or sealing function. In some embodiments, the controller may provide this functionality without the use of a saved profile. In some embodiments, the polishing and/or sealing may occur at the beginning of the brushing session.

Some of the modes may be offered to the user depending on the type of refill attached to the handle. For example, if a refill with a polishing element is attached to the handle, the controller may allow only certain operational modes to the user, e.g. HF/AD. Again, as mentioned previously, the handle and refill may include communication devices which allow the handle to identify the refill. Also, embodiments are contemplated where the personal hygiene device comprises a display which is in signal communication with the handle and the refill. In such embodiments, the display may provide instructions to the handle on what operation modes are available for a particular refill. Additionally, in some embodiments, the handle may recognize the refill and determine which modes are available for the refill. Communication between handles, refills, and/or displays, is described in U.S. Pat. Nos. 7,086,111; 7,673,360; and 7,024,717; and in U.S. Patent Application Publication Nos. 2008/0109973A1; 2010/0170052A1; and 2010/0281636A1. Based on the foregoing, embodiments are contemplated where a user is allowed to select an operational mode from a first set of operation modes for a first refill and a second set of operation modes for a second refill, wherein the first set of operation modes and the second set of operation modes are different. Communication between handle(s), refill(s), and displays, is discussed hereafter.

Handle and Refill

Figure 6:
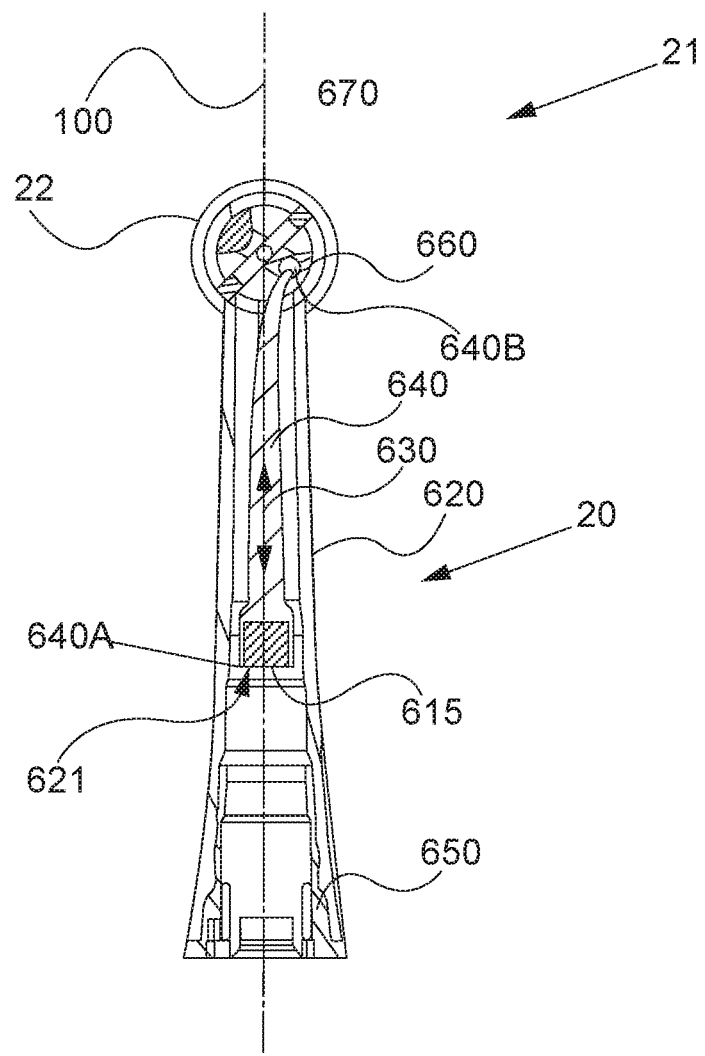
FIG. 6 is a lateral cross section showing the refill of FIG. 1C.

Referring to FIG. 6, the personal care attachment, e.g. refill, 21 comprises the housing 20 described heretofore. Within the attachment housing 20, a drive member 640 resides. The drive member 640 has a proximal end 640A and a distal end 640B. The proximal end 640A may comprise a first attachment element 615, and the distal end 640B may comprise a connection 660. The connection 660 may be coupled to a contact element carrier, e.g. 22, 422. The contact element carrier 22, 422 may be coupled to the attachment housing 20 as described in an application filed in the EPO entitled "ORAL HYGIENE IMPLEMENT AND ORAL HYGIENE DEVICE", filed on Jul. 25, 2011, and having application serial number EP 11006101.7. The contact element carrier 22, 422 may be rotationally coupled to the attachment housing 20 such that when driven, the contact element carrier 22, 422 may move in an oscillating rotating manner.

The first attachment element 615 may comprise a permanent magnet or a magnetizable element such as a block of magnetizable iron or steel. Typically, austenitic steel is not magnetizable, while martensitic or ferritic steel typically is magnetizable. The first attachment element 615 may be disposed within a recess in the proximal end 640A of the drive member 640.

As shown, the drive member 640 may reciprocate generally parallel to the longitudinal axis 100 as shown by arrow 630. Because the connection 660 is eccentric to a pivot 670, the reciprocating motion of the drive member 640 causes the contact element carrier 22, 422 to rotate about the rotational axis 95 (shown in FIG. 1C).

The drive member 640 should be relatively slim to allow it to fit compactly within the attachment housing 20. In some embodiments, the drive member 640 can be less than about 9 mm in diameter, less than about 8 mm in diameter, less than about 7 mm in diameter, less than about 6 mm in diameter, less than about 5 mm in diameter, less than about 4 mm in diameter, less than about 3 mm in diameter, less than about 2 mm in diameter, less than about 1 mm in diameter, or greater than about 1 mm in diameter, greater than about 2 mm in diameter, greater than about 3 mm in diameter, greater than about 4 mm in diameter, greater than about 5 mm in diameter, greater than about 6 mm in diameter, greater than about 7 mm in diameter, greater than about 8 mm in diameter, or any number or any range including or within the values provided. Additionally, the drive member 640 should be mechanically stable and be capable of transmitting forces of about 10 N. Also, the drive member 640 should have a natural frequency of at least 200 Hz, greater than about 225 Hz, greater than about 250 Hz, greater than about 275 Hz, or any number or any range including or within the values provided.

The diameter for the drive member 640 can impact the size of the housing of the refill adversely. For example, if the diameter of the drive member 640 is chosen too high, then the housing for the refill will generally be too large which consumers may perceive as too cumbersome. While smaller diameters for the drive member 640 are desired, the drive member 640 should also be designed to withstand the forces transferred from the drive during operation.

The drive member 640 may comprise any suitable material. Some examples include polyoxymethlylene (POM), polyamide (PA), or polybutylene terephthalate (PBT). In some embodiments, additional reinforcement may be added to the drive member 640. For example, reinforcement fibers, e.g. Kevlar™ fibers may be added to the material of the drive member 640. Any other suitable reinforcement fibers may be added. Additionally, the drive member 640 may comprise a shape which is constructed to reduce the likelihood of buckling. For example, the drive member 640 may comprise a cross section which is in the shape of a cruciform, a Y, or any other suitable shape.

For those embodiments where the drive member 640 comprises a cross sectional shape which is non-circular, the values provided above with regard to the diameter of the drive member 640 may still apply. For example, a drive member 640 comprising a cruciform cross section should not cross the boundary of a circle having a 6 mm diameter, or in some embodiments 5 mm, or 4 mm, or 3 mm, and so on.

As stated previously, in some embodiments, toothbrushes may have an operating frequency of greater than about 120 Hz. With such frequencies, it is important that the personal care attachment, e.g. refill 21, has a resonance frequency which is greater than that of the operating frequency, in some embodiments. If the resonance frequency of the refill 21 is too close to the desired frequency, then during operation, resonance motions may be induced in the refill 21. For example, the refill 21 or the drive member 640 may experience side to side motion. This side to side motion may cause some discomfort to the user and/or additional noise generation during operation.

For those embodiments where resonance motions are not desirable, the resonance frequency of the refill 21 may be greater than about 125 percent of the desired frequency. However, for those refills which are amenable to the HF/AD, FI/AD2, and FV/AV, operational modes, the resonance frequency of the refill may be greater than about 175 percent of the operating frequency, greater than about 200 percent, greater than about 225 percent, greater than about 250 percent, greater than about 275 percent, greater than about 300 percent, or less than or equal to about 300 percent, less than about 275 percent, less than about 250 percent, less than about 225 percent, or any number or range including or within the values provided. For those embodiments where resonance motions are desired, then the refill may be designed to have a resonance frequency which is closer to the desired frequency.

The resonance frequency of the refill 21 or any part thereof may be determined by any suitable method. For example, computer software may be utilized to determine the resonance frequency of the refill 21 or any part thereof. A suitable brand of software is Pro/ENGINEER® Mechanica Wildfire® 4.0.

Figure 7:
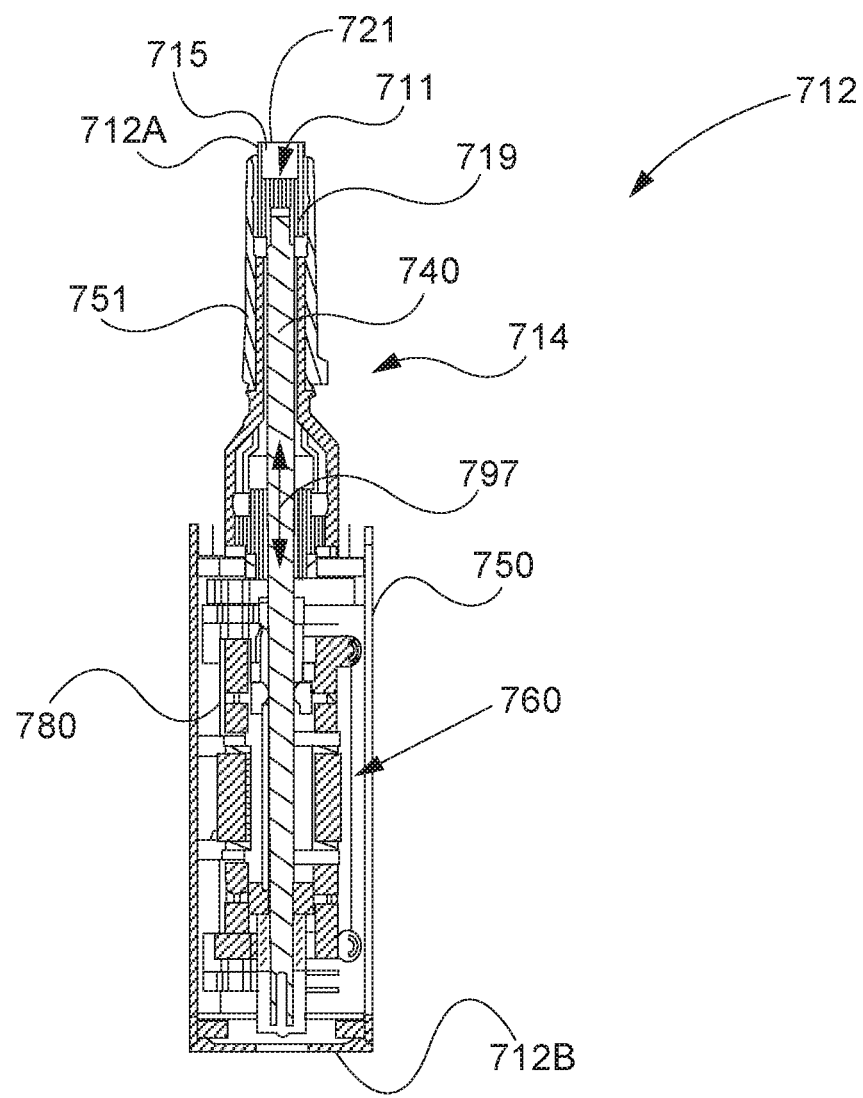
FIG. 7 is a lateral cross section showing an embodiment of a handle.

FIG. 7 shows a longitudinal cut through a handle 712. The handle 712 may be constructed similar to the handle 12 described with regard to FIGS. 1A and 1B. In the shown embodiment, the handle 712 comprises a drive shaft 740 that functions as a movable motor part of a linear drive 760. The linear drive 760 is disposed within the handle 712. During operation, the linear drive 760 cause the drive shaft 740 to reciprocate in a direction which is generally parallel to the longitudinal axis 99 (shown in FIG. 1B). The reciprocating linear movement of the drive shaft 740 as is indicated by double arrow 797. In the shown embodiment, the drive shaft 740 may be prolonged by an extender element 719 that forms a part of the drive shaft 740. The extender element 719 can provide an increase in diameter with respect to the diameter of the drive shaft 740. A recess 711 may be provided in the extender element 719 for accommodating a second attachment element 715.

The second attachment element 715 may be attached to the drive shaft 740 by any suitable method. For example, instead of being accommodated in the extender element 719, the second attachment element 715 may be directly secured at the drive shaft 740. In embodiments where the second attachment element 715 is a magnet, or magnetisable material, the drive shaft 740 may be made at least at its tip portion from a permanent magnetic material, which tip would then form the second attachment element 715.

The second attachment element 715 has a coupling side 721 intended for getting into contact with a respective coupling side 621 (shown in FIG. 6) of the first attachment element 615 of the refill 21 when being attached.

In embodiments where the second attachment element 715 comprise a magnet and/or magnetisable material, the second attachment element 715 may be a cylindrical shape having its cylinder axis essentially oriented parallel to the longitudinal axis 99 (shown in FIG. 1B) of the handle 712. The diameter of the cylinder may be chosen to be about or larger than about 2 mm, larger than about 3 mm, larger than about 4 mm, larger than about 5 mm, or larger than about 6 mm or any individual number or any ranges including or within the values provided.

In those embodiments where the second attachment element 715 is a magnet and/or a magnetisable material, the second attachment element 715 may have any suitable shape. In such embodiments, the second attachment element may have a surface area which is similar to that of those embodiments where the second attachment element 715 is cylindrical in shape.

Any suitable height of the second attachment element 715 may be chosen. For example, the height may be chosen to be about or larger than 2 mm, larger than about 3 mm, larger than about 4 mm, larger than about 5 mm, or larger than about 6 mm, or any number or range within or including these values. In some embodiments, the height may be chosen as large as the diameter. In those embodiments where the first attachment element 615 (shown in FIG. 6) comprises a magnet and/or a magnetisable material, the first attachment element 615 may be constructed similar to the second attachment element 715 described above.

Referring to FIGS. 6 and 7, for those embodiments where the first attachment element 615 and the second attachment element 715 comprise magnets and/or magnetisable material, a magnetizable element (e.g. a magnetizable steel or iron element) can be realized relatively cheap. This aspect may be suitable for an attachment section, e.g. refill 21 intended for disposal after a period of use may then be realized relative cheap. In contrast, a permanent magnet may be more expensive to provide. However, a permanent magnet in the refill 21 together with a permanent magnet in the handle 712 can provide for a higher coupling strength than a permanent magnet and magnetizable element combination at the same construction having the same volume as the permanent magnet combination of the former. As such a trade off exists between the cost versus the strength of connection versus the space requirements. For example, the utilization of a magnetisable element, in order to achieve the strength of connection provided below, may require more volume.

For those embodiments where the first attachement element 615 and the second attachment element 715 comprise magnets and/or magnetisable material, in the attached state, their connection may be designed to withstand a separation force of at least about 2 Newton, of at least about 4 Newton, of at least about 6 Newton, of at least about 8 Newton, of at least about 10 Newton, or any individual number or any range including or within the values provided above. The connection between the first attachment element 615 and the second attachment element 715 as well as their constructions is discussed further in application serial number EP 11006101.7.

At least one benefit of the magnetic coupling of the first attachment element 615 and the second attachment element 715 is that magnetic couplings are not tolerance based. As such, during operation, the magnetic coupling structure proposed heretofore may reduce the sound intensity level produced by the personal care device during operation.

Still referring to FIGS. 6 and 7, the handle 712 comprises a handle housing 750 within which the drive system 760 is disposed. The handle 712 may further comprise an attachment section 714. The attachment section 714 may comprise a second coupling structure 751 which couples to a first coupling structure 650 provided at the refill 21. In some embodiments, the second coupling structure 751 may be rigidly coupled to the housing 750 such that the second coupling structure 751 does not move relative to the housing 750. In such embodiments, the drive shaft 740 provides reciprocal linear motion to the drive member 640 within the refill 21.

Figure 8:
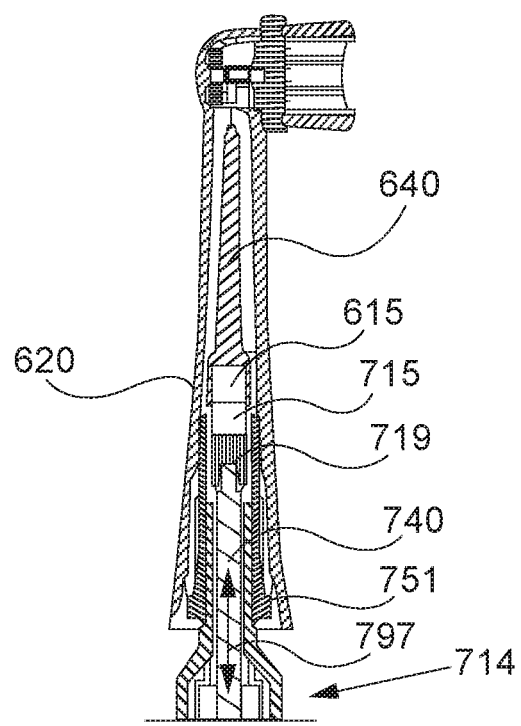
FIG. 8 is a longitudinal cross section showing an interconnection between the refill of FIG. 6 and the handle of FIG. 7.

Referring to FIGS. 6 through 8, in some embodiments, the second coupling structure 751 is, in addition to the drive shaft 740, driven in a reciprocating linear fashion. The second coupling structure 751 may be coupled to a second armature 780 which linearly oscillates with respect to the housing 750. In such embodiments, the drive member 640 is driven as well as the attachment housing 20. For these embodiments, the drive shaft 740 and the second coupling structure 751 may be driven in opposite phases, e.g. 180 degrees out of phase. As such, the drive shaft 740 may be moving in a first direction generally along the longitudinal axis 99 (shown in FIG. 1B) or generally parallel thereto while the second coupling structure 751 is moving in a second direction along or generally parallel to the longitudinal axis 99 (shown in FIG. 1B). The first direction and the second direction can be opposite one another.

At least one advantage of such embodiments is that because of the out of phase linear reciprocation, the vibrations provided to the handle housing 750 because of the movement of the drive shaft 740 may be offset, at least in part, by the portion of the drive system 760 which drives the second coupling structure 751. Reduced vibrations to the handle can similarly lead to less noise generation, i.e. less sound intensity during operation. Additional noise dampening elements are discussed hereafter.

Figure 14:
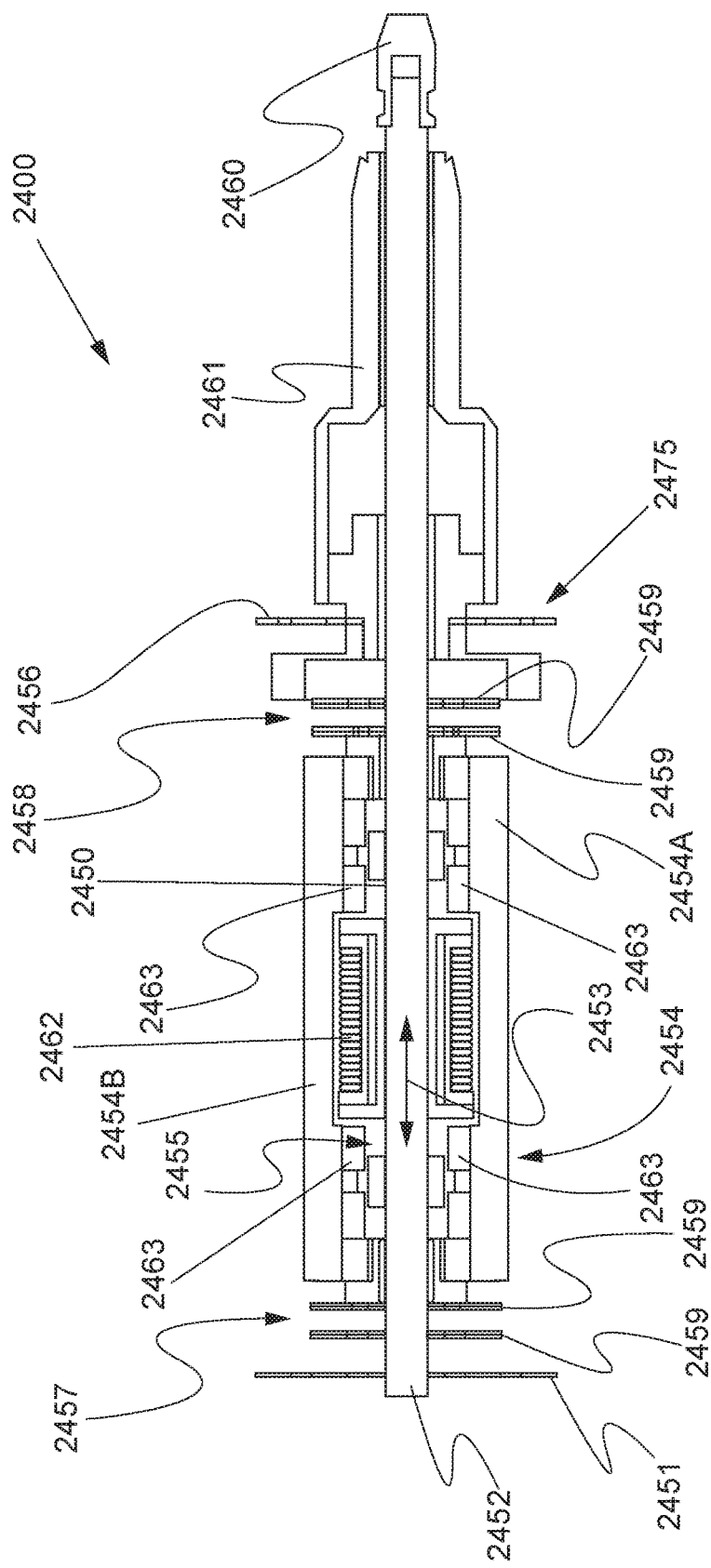
FIG. 14 is a cross section showing another embodiment of a linear motor for use in an embodiment of a personal care device.

Additionally, in some embodiments, a drive system which can be utilized in the present invention may eliminate the need for bush bearings or rolling bearings for support of the drive shaft which can also contribute to a reduction in noise generation during operation. FIG. 14 shows a further embodiment of a linear electric motor. The features described heretofore with regard to FIG. 7 may be combined with the features of FIG. 14 and vice versa.

A drive shaft 2450 may extend along a longitudinal axis of the handle 2400. The drive shaft 2450 is mounted to the housing by a mounting spring 2451. The mounting spring 2451 can be attached to the drive shaft 2450 adjacent a first end 2452 of the drive shaft 2450. The first mounting spring 2451 may be a leaf spring and may generally comprise a circular shape allowing the drive shaft 2450 to perform an oscillating motion in a direction 2453. Due to its design, the mounting spring 2451, in a direction perpendicular to the direction 2453 of motion of the drive shaft 2450, provides a stable support of the drive shaft 2450.

An outer armature 2454 comprises two parts 2454A, 2454B on each side of the drive shaft 2450. The two parts 2454A and 2454B can be attached to each other, such that they move as a single part. The outer armature 2454 can form a channel 2455 between its two halves 2454A and 2454B. The drive shaft 2450 extends through this channel 2455 of the halves 2454A and 2454B of the outer armature 2454. The drive shaft 2450 and the outer armature 2454 can experience an oscillating motion along the same path 2453 during operation.

The outer armature 2454 is mounted via a second mounting spring 2456 to the housing. While the housing is attached to an outer portion of two mounting springs (2451, 2456) the drive shaft 2450 and the outer armature 2454, respectively are mounted to an inner mounting section of the mounting springs 2451, 2456.

The second mounting spring 2456 is attached adjacent a second end 2475 or side of the outer armature 2454 which is opposite to the first end 2452 of the drive shaft 2450. When the drive shaft 2450 and outer armature 2454 move 180 degrees out of phase, the retraction forces transferred from each of the two mounting springs 2451, 2456 onto the housing should compensate each other, at least in part. Namely, the forces transferred to the housing should cancel each other out or at least a portion thereof such that vibrations felt by the user gripping the housing are greatly reduced and/or precluded.

The drive shaft 2450 and outer armature 2454 may be coupled to each other via two coupling springs 2457, 2458. Each of the two coupling springs 2457, 2458 may comprise two leaf springs 2459 which can be leaf springs which are circular in nature (similar to spring 2451). A combination of two springs 2459 for each of the two coupling springs 2457, 2458 may be chosen to be able to easily vary the spring constant of the composed springs 2457, 2458. The drive shaft 2450 is mounted to an inner section of the springs 2459 while the outer armature 2454 is mounted to an outer section of the springs 2459.

A coil 2462 can be attached to the housing providing an interaction with the outer armature 2454. The outer armature 2454 may further comprise a set of four permanent magnets 2463 in order to allow a magnetic and/or electrical coupling between the outer armature 2454 and the coil 2462 at the housing. Embodiments are contemplated where greater than four permanent magnets are utilized. Embodiments are also contemplated where less than four permanent magnets are utilized.

The spring constants of the coupling springs 2457 and 2458 may be chosen such that their resonance frequency corresponds to the oscillation frequency which is imposed by the electric drive consisting of the coil 2462 and the magnets 2463.

In order to provide an oscillating motion, the current flow through the coil 2462 can be controlled such that it is intermittent. The current flow can be interrupted when the drive shaft 2450 and the outer armature 2454 reach the maximum amplitude of their oscillating motion. The coupling springs 2457, 2458 as well as the two mounting springs 2452, 2456 then can force the drive shaft 2450 and the outer armature 2454 back to their respective starting positions.

Each of the drive shaft 2450 and the outer armature 2454 comprises connectors 2460, 2461 for coupling the linear electric motor to functional elements of a household appliance. Such connectors were discussed heretofore with regard to FIGS. 6-8. And, as stated previously, the connectors described in FIGS. 6-8 may be utilized in the embodiment described in FIG. 14.

Additional motors which may be suitable for use in the personal care device of the present invention are described in the following patent applications. Serial Numbers: EP11006065.4; EP11006064.7; EP11006103.3; EP11006067.0; and U.S. Patent Application 61/511,154.

In some embodiments, a drive system comprising a motor providing rotational energy to a refill can be utilized. These motors may similarly accomplish the higher frequencies because they may be utilized as direct drives as opposed to intervening gearing in conventional brushes. Such motors are described in U.S. Patent Application Publication No. US2010/0277013; and EP publication nos. EP2262084; EP2262085;.

Regardless of the motor utilized, the motor should have a larger resonance frequency than the desired frequency. Once a refill is added to the motor, then the resonance of the overall system will generally fall below that of the desired frequency. A difference between the desired frequency and the resonance frequency of the overall system is at least 5 Hz, at least 10 Hz, at least 15 Hz, or at least 20 Hz, or at least 30 Hz, at least 40 Hz, or at least 50 Hz, or any number or any range including or within these values. In some embodiments, the drive frequency is higher than the theoretical resonance frequency of the system.

Theoretical resonance frequency is determined via the following equation.

$$f = \frac{1}{2\pi} * \sqrt{\frac{k}{2I}}$$

Where k=spring constant and I is the mass and/or the mass inertia moment. For example, in the case where the rotational motor is used, no actual springs are present within the motor; however, reluctance forces can act similar to springs and therefore should be accounted for when calculating the resonance frequency. Other suitable methods may be utilized to determine the resonance frequency of the toothbrush or any parts thereof. For example, computer software may be utilized to determine the resonance frequency of toothbrush or any parts thereof, including the refill. A suitable brand of software is Pro/ENGINEER® Mechanica Wildfire® 4.0.

In the rotational motor, the magnetic reluctance force is used as a spring effectively to reset the movement of the drive shaft. The magnets within the motor, which provide the magnetic reluctance force may be designed so that the magnetic reluctance force is linear over an area of plus/minus about 2 mm or plus/minus about 20 degrees of rotation of the shaft. The reluctance force utilized in rotational motors is discussed in additional detail in US2010/0277013; EP publication nos. EP2262084; and EP2262085.

Pumping Effect

As mentioned heretofore, it is believed that beneficial liquid flows occur in the oral cavity where at least a portion of the contact elements have a tip speed of at least about 1.5 m/s. The pressure on the fluid can be described by the following equation.

P=0.5 ρv where ρ=density (assume density of water at standard temperature and pressure) and v=velocity (tip speed). Based on the previous discussion, a first plurality of contact elements adjacent the rotational axis have a lower tip speed than does a second plurality of contact elements which are positioned further outboard of the rotational axis. As such, the velocity pressure exerted on the fluid by the first plurality is less than that of the second plurality. Without being bound by theory, it is believed that the pressure differential from the first plurality to the second plurality tends to act as a pump. For example, it is believed that adjacent the first plurality of contact elements the fluid tends to be sucked up by the first plurality of contact elements. Further, it is believed that the fluid is distributed to the second plurality of contact elements where the fluid is then pumped away from the second plurality of contact elements onto the various oral cavity surfaces. Such pumping of fluid is believed to loosen coatings, e.g. plaque, on the teeth.

In laboratory tests it has been shown that bacteria can be loosened through the shearing force of fluids. It has also been found that not only removal of the bacteria coatings, but also rinsing and control of the composition of the plaque are important. Bacterial dental coatings easily occur in the oral cavity and grow on the gum margin and gum pockets. Bacteria proliferate in these pockets. During their metabolism, the bacteria produce toxins, known as ectotoxins or endotoxins which can cause gum inflammations. It is difficult for one to remove the bacteria as the filaments of conventional brushes cannot penetrate deeply enough into the gum pockets. Through rinsing the cell toxins are removed and the gums recover. Through rinsing, the oxygen partial pressure in the fluid also increases in the gum pockets. In this way anaerobic bacteria which live in the absence of oxygen breed less quickly and are suppressed by less harmful germs. Additionally, many toothpastes contain antibacterial substance(s) in addition to fluorides. Through the flows and built-up pressure toothpastes can penetrate deeper into the biofilm or the pockets and thus achieve a considerably better effect. This effect also leads to recovery of the gum tissue and a reduction in inflammation.

Because the second plurality of contact elements are positioned further away from the rotational axis of the contact element carrier, the second plurality of contact elements generally have more contact with the gum margin. And, as discussed above, it is believed that the fluid is pumped away from the second plurality of contact elements. As such, the pumping of the fluid is believed to loosen bacterial coatings and provide the rinsing effect which aids in the removal of cell toxins and increasing the oxygen partial pressure in the fluid in the gum pockets.

Figure 9:
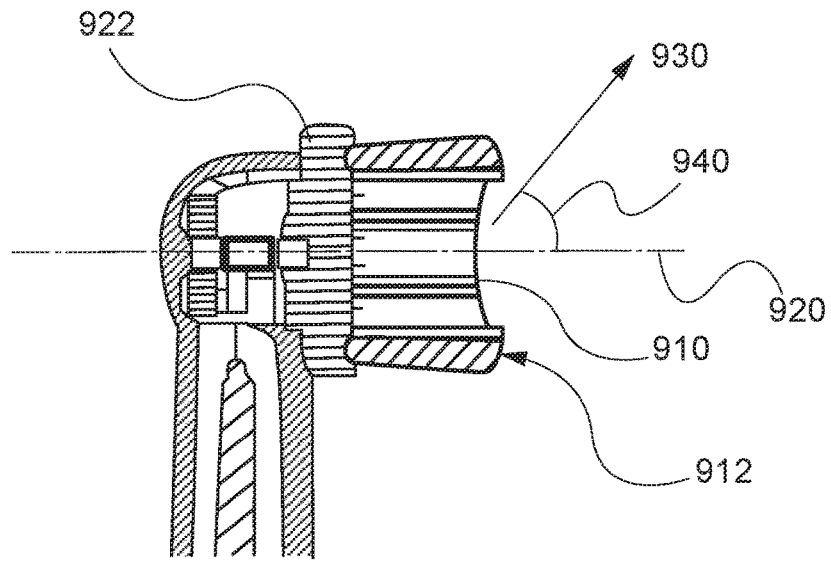
FIG. 9 is a close up view of a partial cross section showing an embodiment of a refill.

In some embodiments, the fluid flow from the contact element carrier may be radial from the contact element carrier. Additionally, in some embodiments, the flow may exit the contact elements at an angle of about 45 degrees. Referring to FIG. 9, a contact element carrier 922 has a rotational axis 920. The contact element carrier 922 may be constructed similar the contact element carriers 22, 422, 922, 1210, described heretofore. Again, it is believed that the fluid flow is drawn to a first plurality of contact elements 910 and is dispersed adjacent a second plurality of contact elements 912. The fluid flow may exit the contact elements at an angle 940 which is greater than about 5 degrees, greater than about 10 degrees, greater than about 20 degrees, greater than about 30 degrees, greater than about 40 degrees, greater than about 45 degrees, greater than about 50 degrees, greater than about 60 degrees, greater than about 70 degrees, greater than about 80 degrees, or less than about 90 degrees, less than about 80 degrees, less than about 70 degrees, less than about 60 degrees, less than about 50 degrees, less than about 45 degrees, less than about 40 degrees, less than about 30 degrees, less than about 20 degrees, less than about 10 degrees, or any number or any range including or within the values provided.

Noise

As stated previously, toothbrushes of the present invention may have an operating frequency of greater than about 120 Hz. Conventional oscillating rotating brushes do not currently operate in this range. There are several potential problems with operating conventional oscillating/rotating toothbrushes at frequencies at or above 120 Hz. As stated previously, the handles of conventional brushes tend to have gearing therein to convert 360 degree motor shaft rotation to a limited displacement angle in a drive shaft. Additionally, the refills for these handles tend to have gearing, springs, etc. for changing the direction of the motion from the drive shaft. A first issue is friction. At higher operating frequencies, the gearing within the handle and/or gearing within the refill would tend to heat up. Eventually, premature failure may occur in either the handle or the refill. A second issue is noise generation. At higher operating frequencies, the gearing in the handle and/or the refill tends to make more noise. The increase in noise generation can be unpleasant to consumers.

For toothbrushes of the present invention, the elimination of gearing in the handle and/or refill can reduce the noise generation at operating frequencies of greater than about 120 Hz. Referring again to FIG. 7, the drive system 760 as configured does not need additional bearings for the shaft 740 or for the second armature 780. Instead leaf springs can be utilized between the shaft 740 and the second armature 780; between the shaft 740 and the housing 750; and between the second armature 780 and the housing 750. Because of the reduced number of moving parts, the handle 712 can produce less noise at higher operating frequencies than does a conventional toothbrush.

Additionally, the drive system 760 is a direct drive system. As such, the shaft 740 connects directly to the refill 21 without any intervening gearing. This helps reduce the sound intensity generation during operation.

Referring back to FIGS. 6 and 7, the refill 21 may similarly help reduce the noise produced by the toothbrush in the assembled state. In conventional refills typically a mechanical coupling such as a snap connection is utilized between the handle and refill. The snap connection has inherently tolerance-based clearances or gaps between the coupling partners so that the coupling partners may move relatively to each other when the respective connection is established between parts driven during operation. Such a mechanical connection is then prone to generate unwanted noise during operation.

In contrast, in some embodiments, the first attachment section 615 attaches to the second attachment section 715 via magnetic attraction. Because a magnetic connection is not tolerance based, the magnetic connection may be prone to produce less noise at operating frequencies of greater than about 120 Hz.

Figure 10:
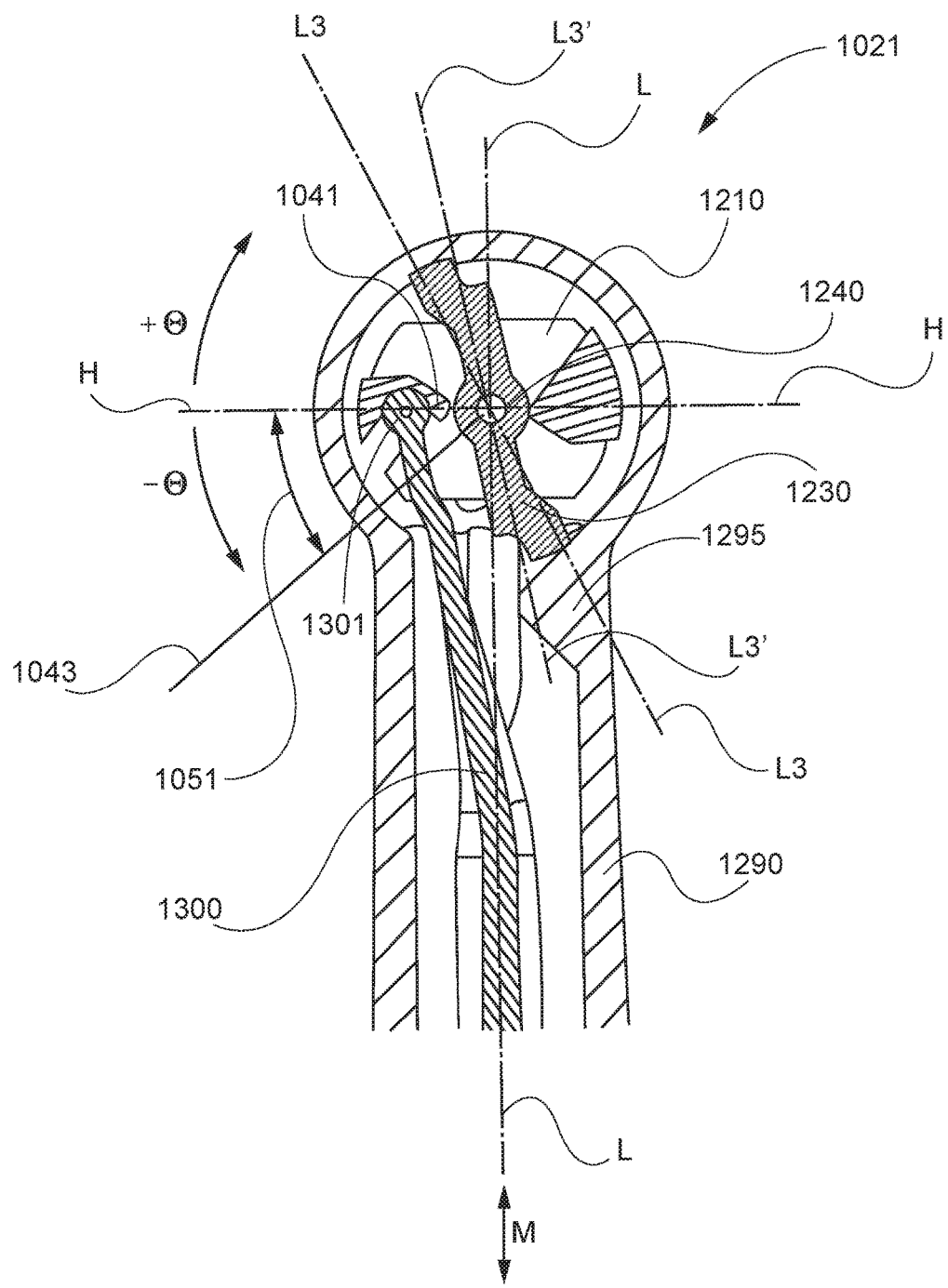
FIG. 10 is a close up view of a lateral cross section showing another embodiment of a refill.

In addition to the attachment mechanism between a refill and handle, a drive mechanism of a refill can contribute to the generation of noise as well. Described below are some additional measures which may reduce the sound intensity levels when implemented in a refill. Accordingly, the features described hereafter may be combined with the features of the refill 21 previously described and vice versa. Referring to FIG. 10, a cross section of a refill 1021 is shown. In some embodiments, the refill 1021 may comprise a shaft element 1300 having a pivot pin 1301 coupled to a carrier 1210 of the functional element of the oral hygiene implement in the horizontal plane H when being in the neutral position.

The horizontal plane H passes through an axle 1240 which is the rotational axis of the contact element carrier 1210. And, the horizontal plane H is perpendicular to the longitudinal axis L of the refill 1021. The longitudinal axis L is the longest dimension of the refill 1021 which bisects the housing 1290 in the plane shown in FIG. 10.

A fixation element 1230 is secured at the housing 1290 at two locations that are opposite with respect to the axle 1240 that is supported in the centre of the fixation element 1230. The housing 1290 may comprise an inwardly extending portion 1295 to which the fixation element 1230 is supported to generally allow for a small angular offset between a general extension direction L3 of the fixation element 1230 and a longitudinal extension direction L of the oral hygiene implement (the extension direction L3 is defined by the two mounting locations).

In the shown embodiment, the fixation element 1230 does not extend symmetrically along the connecting line L3 between the two mounting locations. Instead, the fixation element 1230 is curved in such a manner that it is concave with respect to the direction from which the pivot pin 1301 approaches when moving in positive angular direction (i.e. toward the maximum oscillation angle +θ). This allows for a larger maximum oscillation angle. The effective extension direction of the fixation element 1230 is indicated by L3'. As is shown, the fixation element 1230 may be symmetrically curved with respect to the centre axis defined by the axle 1240. Here, curved shall include stepped designs of the fixation element 1230.

It was discovered that the orientation of the pivot pin 1301 with respect to the horizontal axis H can contribute to the noise generated when the refill 1021 is in operation. For example, an imaginary radial arm 1041 is defined by a distance between a center point of the pivot pin 1301 and a center point of the axle 1240. When the radial arm 1041 is colinear with the horizontal axis H, in the neutral position of the system, the relative noise generation during operation is low. However, when the radial arm 1041 is moved to away from the horizontal axis H, noise generation tends to increase during operation. If the radial arm 1041 were positioned such that the radial arm 1041 were co-linear with an offset arm 1043 an angle 1051 would exist between the radial arm 1041 and the horizontal axis H. In order to decrease the noise generated by the refill 1021 during operation, the angle 1051 can be about zero degrees, greater than about 2 degrees, greater than about 4 degrees, greater than about 5 degrees, greater than about 8 degrees, greater than about 10 degrees, greater than about 15 degrees, greater than about 20 degrees, greater than about 25 degrees, greater than about 30 degrees, greater than about 35 degrees, greater than about 40 degrees, or less than about 40 degrees, less than about 35 degrees, less than about 25 degrees, less than about 20 degrees, less than about 15 degrees, less than about 10 degrees, less than about 5 degrees, less than about 2 degrees, or any number or any range within or including the values provided above.

The angle described above is not limited to being subjacent to the horizontal axis H. In some embodiments, the angle between the radial arm 1041 and the horizontal axis H can be superjacent to the horizontal axis H.

Without being bound by theory, it is believed that for angles greater than about 45 degrees, the forces acting on the pivot pin 1301 are split in a disadvantageous manner. For example, consider that the force acting on the shaft element 1300 tends to act along the longitudinal axis L of the refill 1021. For orientations of the pivot pin greater than 45 degrees, less than half of the applied force to the pivot pin 1301 is being utilized to move in a direction which is parallel to the longitudinal axis L. As such, more than half of the applied force is wasted. It is believed that this wasted force creates additional heat and noise.

Additional measures may be taken in the handle 712 to reduce the noise emitted by the toothbrush. For example, a noise abatement material may be positioned between the second armature 780 and the housing 750. For example, a lead tape may be placed within the housing in order to reduce the noise output from the brush. Additionally, in embodiments where the second armature 780 does not move relative to the housing 750, the lead tape may also serve to reduce the vibrations experienced by a user during use.

Various prototypes and conventional power toothbrushes were tested to determine noise levels. Each of the toothbrushes were tested in accordance with the test method as described below. In a first comparison, a conventional power toothbrush handle without a refill was tested at its normal operating speed and then boosted to a drive frequency which is comparable to that of the prototypes described in the embodiments herein. Table 1 provides the results of the testing.

The conventional brushes tested comprised handles and refills. The conventional handles included rotational motors. The conventional handles tested are similar to the Oral-B® Professional Care 1000 and Oral-B® Professional Care 3000 series of power handles. The refills used in the testing for the conventional handles as well as the prototype handles with the rotational motors was the Oral-B® Precision Clean.

TABLE 1

| Type of handle | Tested operating frequency | Sound level dB(A) |
|---|---|---|
| Conventional | 88 Hz | 72.4 |
| Conventional | 172 Hz | 82.9 |
| Prototype with rotational motor without idle run state | 163 Hz | 55.3 |
| Prototype with rotational motor with idle run state | 163 Hz | 40.3 |
| Prototype with linear motor without idle run state | 152 Hz | 42 |
| Prototype with linear motor with idle run state | 152 Hz | 44.2 |

As shown in Table 1, both the prototypes either with a rotational motor or a linear motor produced lower noise in normal operation than did the conventional brush at either operating frequency. The conventional toothbrush handle was modified for the testing at 172 Hz. Specifically, the power source for the motor was modified to provide the requisite voltage in order to achieve the higher operating frequency in the conventional toothbrush handle.

It is expected based upon the values that for frequencies below 163 Hz and 152 Hz that the prototypes tested would produce lower sound intensities. Based on the findings in Table 1, the handles constructed in accordance with the present invention may operate at frequencies greater than 120 Hz, and as described previously, while producing less than about 80 dB(A) sound intensity. In some embodiments, the handles may operate at a frequency of greater than about 120 Hz while producing a sound intensity of less than about 75 dB(A), less than about 70 dB(A), less than about 65 dB(A), less than about 60 dB(A), less than about 55 dB(A), less than about 50 dB(A), less than about 45 dB(A), less than about 40 dB(A), less than about 35 dB(A), less than about 30 dB(A), or greater than about 30 dB(A), greater than about 35 dB(A), greater than about 40 dB(A), greater than about 45 dB(A), greater than about 50 dB(A), greater than about 55 dB(A), greater than about 60 dB(A), greater than about 65 dB(A), greater than about 70 dB(A), or any number or any range within or including these values.

Also shown in Table 1, at least one of the rotational motor prototypes and one of the linear motor prototypes include the idle run state feature. For the idle run state feature, the frequency was kept at normal operating frequency; however, the amplitude exhibited by the drive shaft was reduced below that of the respective prototypes without the idle run state feature. The prototype with the rotational motor exhibited the behaviour that would generally be expected, i.e. with decreased amplitude decreased noise. The values for the rotational motor prototype reflect this, i.e. 55.3 dB(a) versus 40.3 dB(A).

Regarding the linear drive prototypes, the sound intensity between the idle run state prototype and the non-idle run state prototype is a marginal difference. It is believed that because of the extremely low sound intensity level of the non-idle run state prototype, the implementation of the idle run state did not appear to provide additional reduction in sound intensity. Additionally, background noise can have a larger impact on low sound intensities.

Additional noise testing was performed on conventional toothbrushes and prototypes. As shown in Table 2, the toothbrush handles were tested with refills attached thereto in both an unloaded and a loaded condition. The load applied to the refill in the loaded condition was 2 N. Also, the same type of refill used for the conventional toothbrush was used on the rotational motor prototypes; however, a prototype refill was utilized on the linear motor prototypes.

TABLE 2

| Type of handle | Tested operating frequency | Sound level dB(A) - unloaded | Sound level dB(A) - 2N load |
|---|---|---|---|
| Conventional | 82 Hz | 66.5 dB(A) | 66.5 dB(A) |
| Conventional | 153 Hz | 77.9 dB(A) | 76.5 dB(A) |
| Prototype with rotational motor without idle run state | 164 Hz | 65.8 dB(A) | 63.3 dB(A) |
| Prototype with rotational motor with idle run state | 163 Hz | 61 dB(A) | 62.8 dB(A) |
| Prototype with linear motor without idle run state | 152 Hz | 62.3 dB(A) | 58.8 dB(A) |
| Prototype with linear motor with idle run state | 152 Hz | 52 dB(A) | 60 dB(A) |

Regarding the test results of the refill in the unloaded state, as shown in Table 2, with the refill attached, the sound intensities for the two conventional toothbrush handles dropped compared to the values of Table 1. It is believed that the attachment of the refill to the conventional toothbrush handles may reduce the existence of some of the tolerance based features of the handle. Accordingly, the sound intensity drops with the attachment of the refill.

In the case of the tested prototypes the opposite occurred. With the attachment of the refills, the sound intensities actually increased. However, as stated previously, in an effort to reduce the sound intensity produced by the handles constructed in accordance with the present invention, the existence of tolerance based elements, e.g. bearings, has been reduced or eliminated. As such, the attachment of the refill to the prototypes does not have the same effect as the attachment of a refill to a conventional handle does. Namely, the attachment of the refill to the prototype handle does not reduce the existence of tolerances because tolerance based elements have been reduced and/or eliminated in the prototype handles.

The refills constructed in accordance with the embodiments described herein, in an unloaded state, should add no more than about 8 dB(A), no more than about 10 dB(A), no more than about 12 dB(A) no more than about 14 dB(A), no more than about 16 dB(A), no more than about 18 dB(A), or no more than about 20 dB(A), or any number or any range including or within the values provided.

With an applied load of 2 N, the conventional brush having an operating frequency of 153 Hz, emitted less sound intensity than in the unloaded state. It is believed that the conventional refill utilized on the conventional handle similarly includes tolerance based elements as discussed heretofore. As such, the application of the 2 N load is believed to have decreased the size of the tolerances and therefore reduced the sound intensity.

Similarly, the rotational motor prototype, not having the idle run state feature utilized similar refills as the conventional brush. Specifically, conventional refills were utilized on the rotational motor prototypes. As such, a decrease in sound intensity was also seen with the applied load of 2N. Regarding the rotational motor prototype with the idle run state feature, recall that in the unloaded state, the amplitude is reduced. In contrast, an applied load of 2 N causes the drive system to increase the amplitude to the normal run state thereby increasing the sound intensity.

Regarding the prototypes having the linear motors, the prototype without idle run state saw a decrease in the sound intensity under load. Recall however that the without idle run state, this prototype was operating at a desired frequency in a desired amplitude range even under no load. As such, when the load was applied, the amplitude was decreased. The decrease in amplitude may explain the reduction in sound intensity. For the prototype having the idle run state feature, an increase in sound intensity was seen. Recall that with the idle run state, when a load is sensed, the amplitude is boosted to be within the desired amplitude range. As such, an increase in sound intensity occurred.

Device Communication

Figure 13:
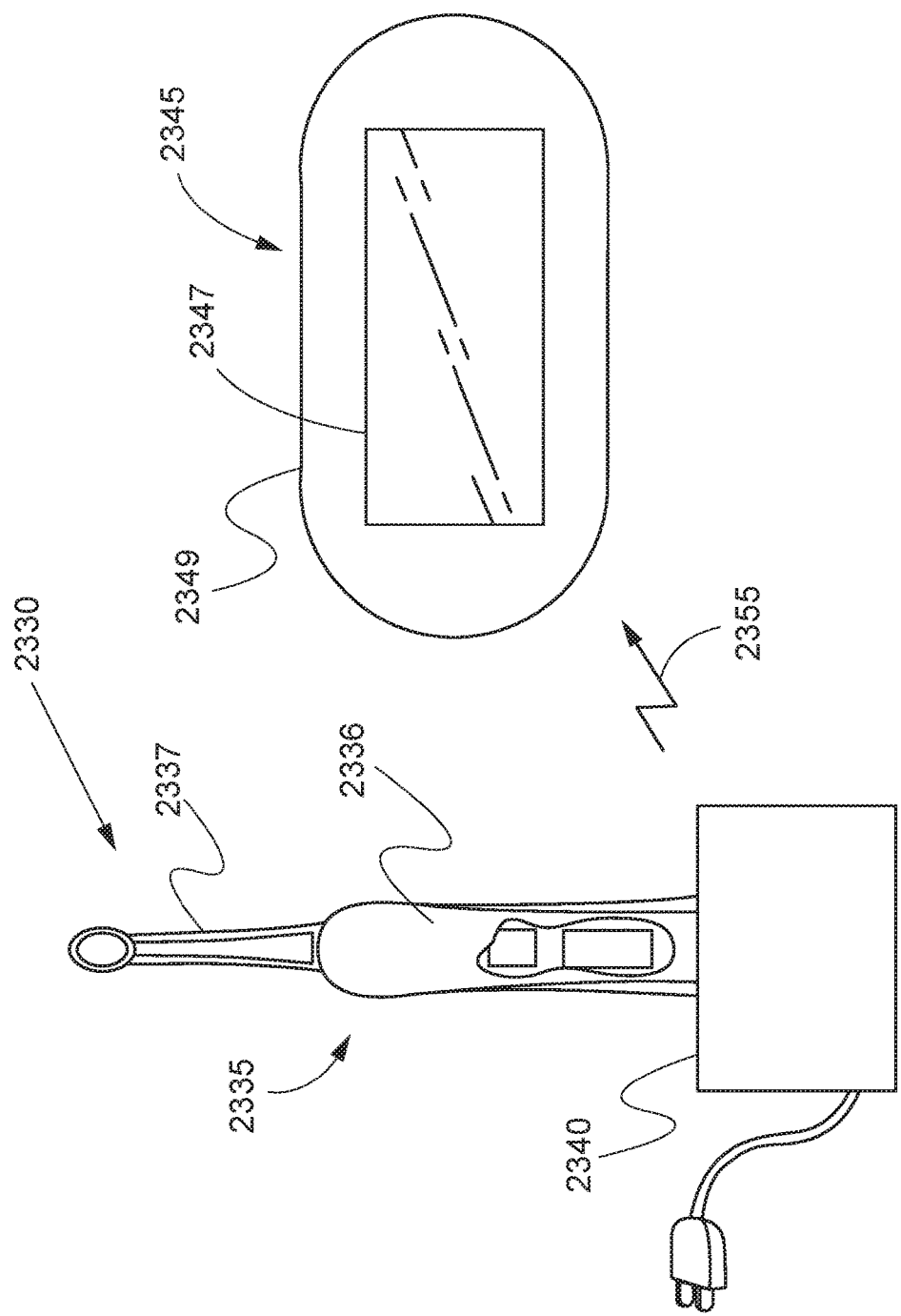
FIG. 13 is a schematic representation showing wireless communication between/among a personal care device and a display.

As stated previously, handles, refills, etc. may communicate with an external display. As shown in FIG. 13, an oral care system 2330 comprising an electric toothbrush 2335, a base 2340 for receiving the electric toothbrush 2335, and a visual and/or audio display 2345 that is in continuous and/or intermittent data communication with the electric toothbrush 2335 and/or the base 2340 before, during, and/or after use by a consumer of the electric toothbrush 2335. The toothbrush 2335 may comprise a handle 2336 and a refill 2337. Embodiments are contemplated where the display 2345 comprises a wireless communication link with the handle 2336, and/or the refit 2337.

The oral care system 2330 can use a variety of arrangements, singly or in combination, to implement data communication between the display 2345 and the electric toothbrush 2335 and/or base 2340. In one embodiment, the toothbrush 2335 and/or the base 2340 are in wireless communication with the display 2345 via wireless data link 2355. The wireless data link 2355 may be based upon a suitable short range radio frequency communication technology, such as Bluetooth, WiFi (802.11 based or the like) or another type of radio frequency link, such as wireless USB at 2.4 GHz. For radio transmissions, an antenna can be mounted on a printed circuit board (PCB) disposed in the electric toothbrush 2335, base 2340, sleeve, and/or the display 2345.

For infrared (IR) transmissions, one or more IR transmitter diodes can be mounted in the electrical toothbrush 2335, the handle 2336, the base 2340, the sleeve, the refill 2337, and/or the display 2345. An IR wavelength suitable for use with the present invention is 950 nm modulated at 36 KHz.

Other wireless data communication technologies may be used such as, for example, radio frequency transmission or cellular transmission. In some embodiments, a plurality of oral care products may be in data communication with the electric toothbrush 2335, the base 2340 and/or the display 2345, as previously described. The data transfer can be one-way and/or two-way, continuous and/or intermittent, modulated, or any combination of the foregoing, between the display 2345, the base 2340, electric toothbrush 2335, the handle 2336, the refill 2337, and/or any other personal care product. As previously described, the display 2345 can be configured to communicate using one or more types (e.g., IP wireless radio, hard-wired, etc.) of data communication methods, and the same display 2345 can employ different types of data communication methods with different personal care products.

In some embodiments, a data reader can be associated with a toothbrush in variety of ways. For example, the data reader can be provided in the toothbrush handle 2336, a charging station, e.g. base 2340, a detached display 2355, or other detached device, a toothbrush stand, etc. In one embodiment, a data transmitter can be provided as a radio frequency identification (RFID) tag that can be used to transmit data between the personal care product, e.g. refill 2337, and the display 2345. As known in the art, an RFID tag comprises an electronic chip that contains encoded information and an antenna that transmits and/or receives information or data (including information stored by the chip) using radio waves. A reader is used to decode the data transmitted from the RFID tag. The RFID tag may be provided without an internal power supply, and the minute electrical current induced in the antenna by the incoming radio frequency signal from the reader provides just enough power for the integrated circuit in the tag to power up and transmit a response to the reader. The RFID tag can be a read only tag or a read/write tag. The data stored by a read only tag is pre-programmed, typically by a manufacturer, in non-volatile memory and cannot be changed by a later user of the personal care product or system. The data stored by a read/write tag can be later rewritten to the tag during later use, typically by the reader.

The data stored by the RFID tag or other data transmitters/communicators can be quite varied, including any personal care information. Some of the categories of data includes product identification data (e.g., the brand name or product name) and product usage or regimen data (e.g., usage time, such as 1 minute regimen for a rinse, text or graphical instructions concerning product usage), one or more rewards, and component or product replacement data (e.g., number of times or length of time that a component or product can be used before it should be replaced). Instructional images, text, or data can be particularly useful for children in establishing appropriate brushing regimens.

Data can be directly displayed on the display 2345 or can be used as an input to the processor for a function or feature of the display 2345. For example, an RFID tag for the refill 2337 could store usage data that states the recommended modes of operation. For example, a refill having polishing elements may be amenable to the HF/AD mode. As such, when the refill is coupled to the handle, a processor in the handle may restrict the number of modes available for the refill being utilized. As another example, a refill design for tongue cleaning may be amenable to a tongue cleaning mode but not the TS mode. As such, when the refill is coupled to the handle, the processor. The RFID tag can transmit the usage data to a reader associated with the display 2345.

A data transmitter is a device or component that actively transmits data to a data reader. An RFID tag is an example of a data transmitter. A data communicator is a device or component that may or may not actively transmit data but which has data that is capable of being detected. While a data transmitter, such as an RFID tag, is a type of date communicator, a data communicator need not necessarily actively transmit data. Examples of data communicators that contain data that that may be detected or read by a data reader but which do not actively transmit data include a bar code (wherein the bar code reader is the data reader), a spotcode, or a hall effect magnet (wherein the hall effect sensor is the data reader). Thus, as will be appreciated, the phrases "data communicators", "data transmitters" and "data readers" are intended to encompass a wide variety of devices and arrangements for the transmission, communication, and/or detection of a variety of analog or digital data, including the mere detection of the presence of a data communicator. The phrase "data communication" is intended to encompass all the methods and forms by which data may be transmitted, communicated, and/or detected by a devices of the present invention, including data readers, data transmitters, data communicators, as well as data communication between a two components such as a display and an electric toothbrush.

The term "data" is intended to refer to any digital or analog information in any form that is transferred or communicated between two devices or components. Data may include any data actively transmitted by a data transmitter and/or data that is passively detected by a data reader. Data may include ones and zeroes if the data that is communicated is digital. In another embodiment, data could be a series of digits, such as 12345678, wherein each digit could represent information about a characteristic of an oral care device (e.g., for a manual toothbrush, the first digit could represent the brushing time in minutes, the second digit could represent the number of months until the brush should be replaced, the third and fourth digits could represent a type unique reward, etc.). Data may include the arrangement of optical elements (e.g., a bar code) that represent information. Data may include the presence or absence of electromagnetic energy (e.g., such as a magnetic field) and the like. The data may be interpreted or decoded by the processor. For instance, where the data is a series of digits, such as 12345678, the processor and/or associated memory could comprise a set of instructions that would be able to decode or interpret the data to determine what information is represented by the data.

The data communication between a data communicator and a data reader can occur at a variety time before, during, or after an oral care regimen and can be sequential or modulated. For instance, each of a plurality of oral care products having an RFID tag might be moved in proximity of the display 2345 so that the RFID tag can transmit its data to a reader that is part of the display 2345, the sleeve, or another component of one of the personal care systems. The data transmission can occur prior to each usage of the oral care product or may only need to occur once, such as the first time the product is used, and the data is thereafter stored by the reader or a component associated with the reader. A counter can be implemented that stores the number of times that data is transmitted from the RFID tag to the reader for each personal care product.

The display 2345 can provide the user with a plethora of information. For example, in some embodiments, the display 2345 may provide an indication to the user of the modes that are available for a particular refill. Additionally, the display 2345 may provide a visual indication of which modes the user has used previously with the current refill or which modes the user has used previously with several refills. Additional information that can be provide by the display is discussed in U.S. Pat. Nos. 7,086,111; 7,673,360; and 7,024,717; and in U.S. Patent Application Publication Nos. 2008/0109973A1; 2010/0170052A1; and 2010/0281636A1. Additionally, communication between handles, refills, and/or displays is also discussed in U.S. Pat. Nos. 7,086,111; 7,673,360; and 7,024,717; and in U.S. Patent Application Publication Nos. 2008/0109973A1; 2010/0170052A1; and 2010/0281636A1.

Test Methods:

Oscillation Displacement Angle:

Referring to FIG. 11A, a laser 1110, a lens 1130, light sensors 1120, 1121 and a reflective surface 1150, are required. The laser 1110 is manufactured by Global Laser, HRST-Teilenummer 5200-56-000. The laser 1110 is 5 mW with a wavelength of 635 nm in accordance with EN60825, and the laser 1110 is a class 2M.

The lens 1130 has a 30 mm diameter and is made from PMMA (plexiglass) and has polished surfaces. The lens 1130 is positioned such that the light emitted from the laser 1110 bisects the thickness of the lens 1130 and impinges on a point on the circumference of the lens which corresponds to the diameter and not merely a chord of the lens. The lens 1130 should focus and split the beam into a line which is generally perpendicular to the plane of the sheet upon which FIG. 11C is shown.

Figure 11B:
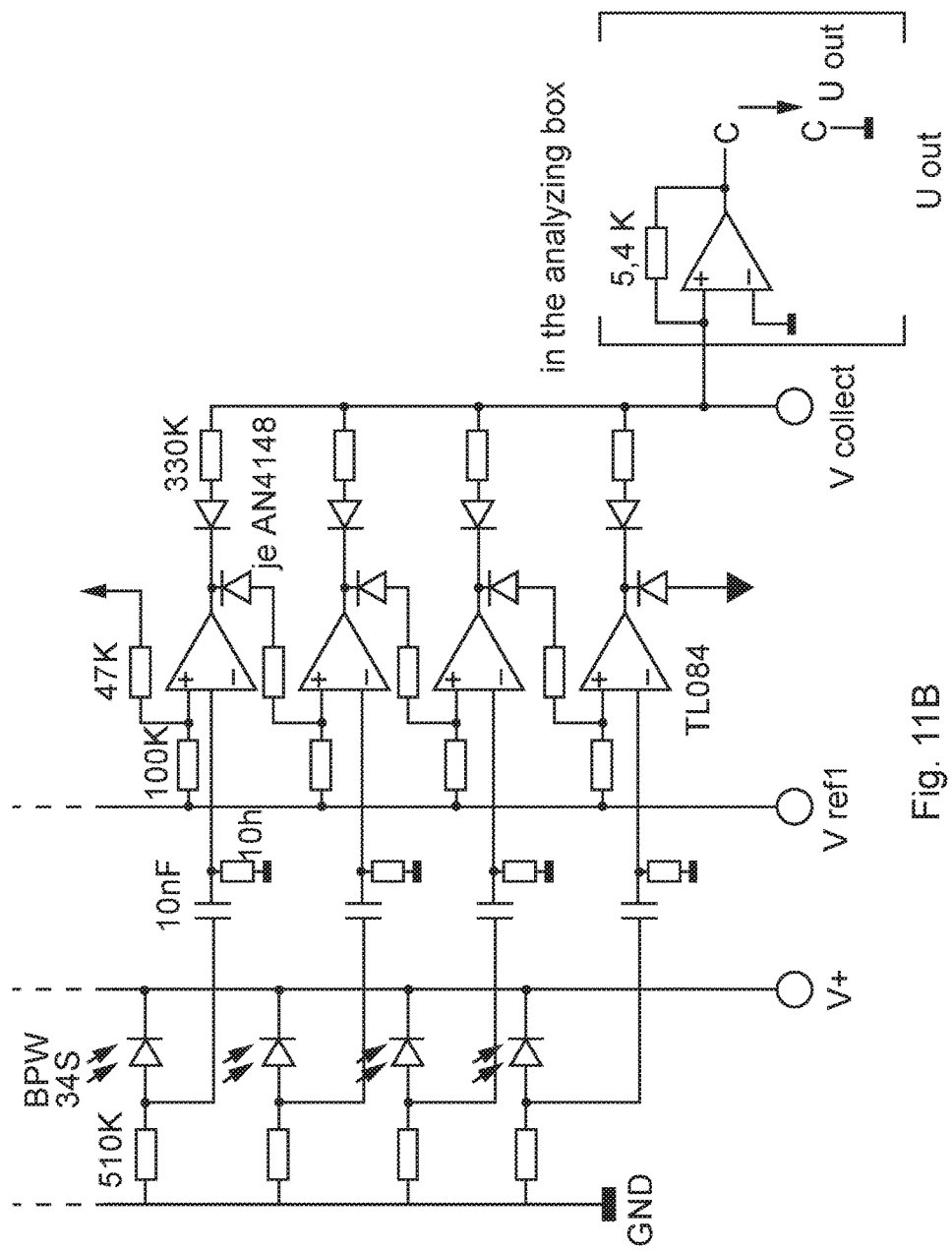
FIG. 11B is a circuit diagram showing a plurality of photodiodes and their arrangement for the sensor arrays in the test set up of FIG. 11A.

The light sensors 1120 and 1121 each comprise an array of 56 photodiodes without filters which are manufactured by Osram Opto Semiconductors. The photo diodes are arranged as shown in FIG. 11B and mounted on a printed circuit board (PCB). The PCB forms the front-facing surface 1120A and 1121A of the sensors 1120 and 1121. The light sensors 1120 and 1121 should be positioned equidistant from a horizontal bisecting line 1190 of the lens 1130. Additionally, the bisecting line 1190 should be perpendicular to the reflective surface 1150 in the neutral position. So as positioned, 56 photodiodes are positioned above the the reflective surface 1150 and 56 photodiodes below the reflective surface 1150.

A center point of the contact element carrier 1140 should be spaced from a center point of the lens 1130 by a distance 1170 of 44 mm. Similarly, the center point of the contact element carrier 1140 should be spaced from front-facing surface 1120A and front-facing surface 1121A of the light sensors 1120 and 1121 by a distance 1160 of 89 mm. If the contact carrier element being tested has an elliptical shape, then the center point is where the intersection of the minor axis and the major axis occur. For other shapes, the geometric center can be utilized as the centerpoint.

The photodiodes of FIG. 11B should be in signal communication with an evaluator which then sends information to a computer for storage and/or analysis. The circuit includes a high pass RC filter for filtering out daylight.

The reflective surface 1150 may be any suitable reflective surface; however, the material selected should reflect as close to 100 percent of the light as possible and the material should have sufficient rigidity such that during testing, no deflection of the reflective surface occurs. Additionally, the mass of the reflective surface 1150 should be kept small to ensure that that mass of the reflective surface 1150 has little if any impact on the performance of the toothbrush being tested. A small sheet of metal, polished, is utilized having a size of 3 mm by 11 mm. The reflective surface 1150 is placed at 90 degrees to a long direction of the refill.

A suitable frame should be constructed to hold a toothbrush and toothbrush refill to be tested such that during operation, the toothbrush and refill remain fixed horizontally and vertically. As shown, a contact element carrier 1140 to be tested should be positioned such that the contact elements thereon are positioned as shown, into the plane of the sheet of FIG. 11A. The reflective surface 1150 should be attached tangent to the contact carrier element 1140 and positioned between the contact carrier element 1140 and the lens. While the toothbrush (the contact element carrier 1140) are in an unpowered state, the reflective surface 1150 should be attached normal to a diameter of the contact element carrier 1140.

If the contact element carrier 1140 comprises a shape which is other than circular, then the refill to be tested should be attached to the handle to be tested and placed in the frame. The laser 1110 should be powered on and the toothbrush should remain off. Where the laser line from the lens 1130 crosses the contact element carrier 1140, the reflecting surface 1150 is attached tangentially. Recall, that the reflecting surface 1150 should be attached such that the bisecting line 1190 is perpendicular to the reflecting surface 1150.

As shown in FIG. 11C, a toothbrush to be tested 1100 has a refill attached thereto. The contact element carrier 1140 of the refill has the reflective surface 1150 as described heretofore. Additionally, a plastic plate 1119 can be placed in contact with a contact element field 1118 when the oscillation displacement angle is desired under loaded conditions. When the oscillation displacement angle under no load is desired, then the plate should not be in contact with the contact element field 1118. For loaded conditions, the linear stepper motor 1115 should be advanced in increments of 0.2 mm until the plastic plate 1119 applies the desired force on the contact element field 1118 while the toothbrush is an operating state. The force sensor is manufactured by TesT GmbH and has a model no. K320.20N.

The laser 1110, force sensor, should be calibrated in accordance with the manufacturer's recommendations prior to testing. Regarding the light sensors 1120 and 1121 these too should be calibrated. The light sensors can be calibrated by performing static tests. A device having a mirror is placed in the frame and positioned at a particular angle which can be measured physically without the use of the light sensors. The device is kept static and the laser 1110 is powered on. Data is collected and analyzed to determine if the measured angle corresponds with the angle derived from the light sensor 1120 or 1121 data input. The device should be rotated to test at least three different angles for each of the sensors 1120 and 1121. If discrepancies exist between the measured angle and the derived angle, the evaluation parameters (software) should be adjusted. Repeat calibration steps as required until the measured angle and the derived angle are within five percent of each other.

The computer should be equipped with appropriate software to analyze the voltages transmitted by the photodiodes. A suitable software for this purpose is LabView VI.

Place the toothbrush and refill to be tested in the frame where the refill is properly attached to the toothbrush. The refill should be equipped with the reflecting surface 1150 as described heretofore. Fix toothbrush to the test frame to ensure that the toothbrush does not move relative to the test frame during testing. Turn on the laser 1110. Turn on the sensor 1120 to make sure that the computer connected to the light sensors 1120 and 1121 is in a state for recording data. Adjust toothbrush and/or frame as required such that the light transmitted from the lens 1130 achieves the necessary requisites above. Turn on the toothbrush to the desired mode for which the oscillation displacement angle is to be tested. Record data.

Ensure that a sufficient number of data points are collected and averages taken in order to validate the oscillation displacement angle measurement.

Sound Intensity

All sound measurements were taken in accordance with CEI/IEC 60704-1: 1997, entitled "Household and similar electrical applicances—Test code for the determination of airborne acoustical noise", which is incorporated herein by reference in its entirety. Any deviations from the test method are described below. Specifically, those portions of the test method referring to hand-held appliances are to be utilized.

Figure 12:
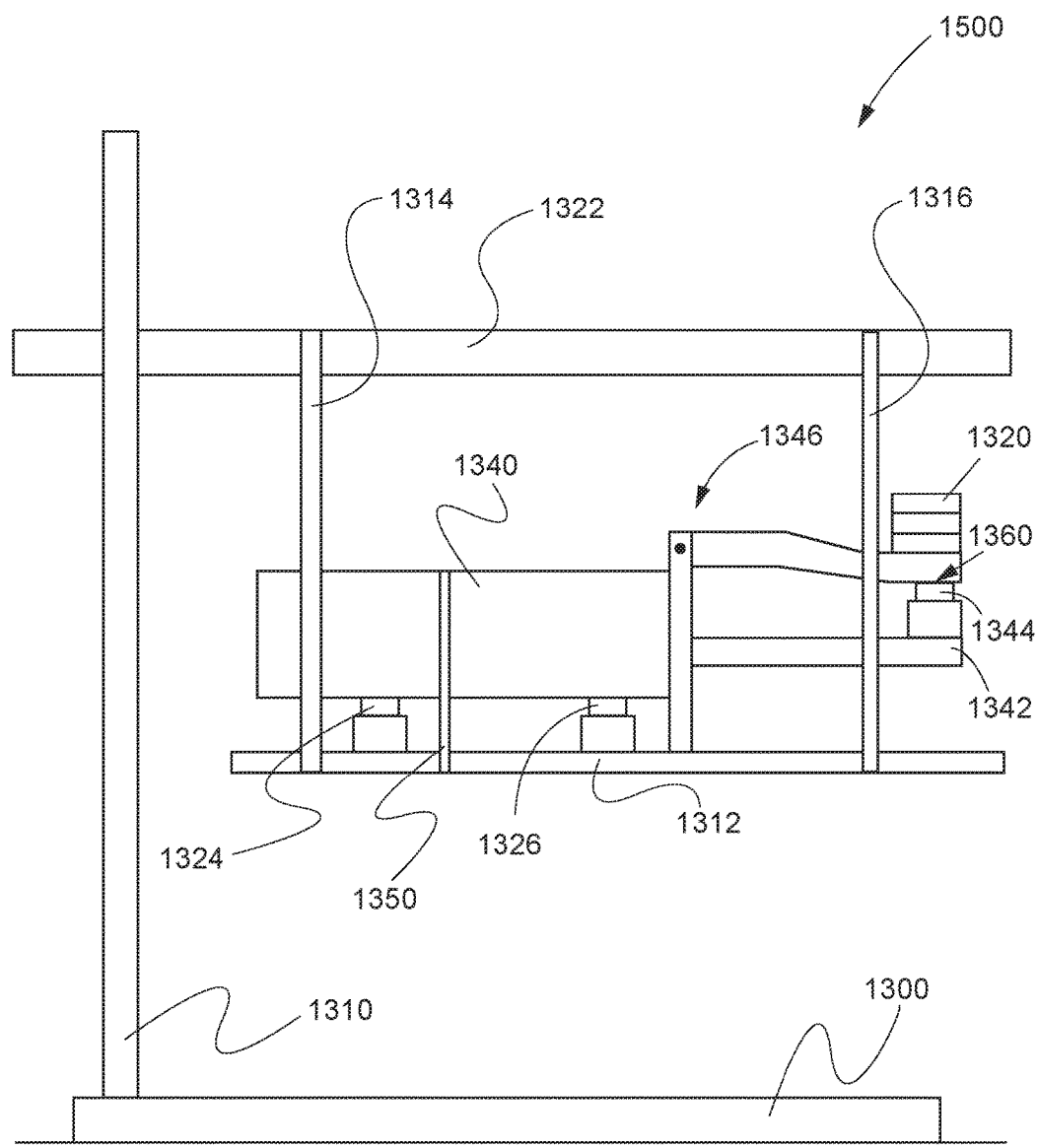
FIG. 12 is an elevation view showing a test stand for supporting hand held devices for sound intensity testing.

All measurements should be done in a semi-anechoic room. A sound meter as provided in the incorporated test methodology is required. Also, additional instrumentation as provided in the incorporated test methodology. The sound meter should be calibrated in accordance with the recommendations of the manufacturer prior to testing. A test stand as shown in FIG. 12 constructed in accordance with section 6.5.2 of the incorporated test methodology.

A test stand 1500 has a base 1300 placed on an intermediate resilient means between the base 1300 and the floor. A rigid vertical support 1310 is rigidly connected to the base 1300. A rigid horizontal support 1322 is fixed to the rigid vertical support 1310 such that the rigid horizontal support 1322 does not move during testing. An intermediate base 1312 is disposed between the base 1300 and the horizontal support 1322 and is adjusted such that when the toothbrush is placed on the intermediate base 1312, the brush head has a distance of approximately 25 cm from the floor.

The intermediate base 1312 is suspended from the horizontal support 1322 by resilient elements 1314 and 1316. The intermediate support 1312 comprises a first resilient support 1324 and a second resilient support 1326 for supporting a toothbrush 1340 to be tested. The first and second resilient supports 1324 and 1326, respectively, should be spaced such that the toothbrush 1340 remains stationary with respect to the intermediate support 1312 during testing. In an effort to reduce any movement between the toothbrush 1340 and the intermediate support 1312, resilient element 1350 may be utilized. Additional resilient elements may be utilized in order to fix the toothbrush 1340 to the intermediate support 1312.

The intermediate support 1312 also has a load support harness 1346 for applying loads to contact element fields 1344 on refills 1342. The load support harness 1346 should have a smooth bottom surface 1360 and a means for securing a load 1320 to the load support harness such that the applied load 1320 does not move with respect to the load support harness 1346 during testing.

The toothbrush to be tested should be placed in the test stand 1500 as described above such that the toothbrush does not move relative to the intermediate support 1312 during testing. If an applied load is required for testing, the load support harness 1346 should be placed in contact with the contact element field prior to beginning the test. Then the appropriate load 1320 should be placed on the load support harness 1346 and be secured thereto such that the load 1320 does not move relative to the load support harness 1346 during testing.

The handles described herein may be any suitable material. Some examples of suitable material include. Additionally, the handles described herein may comprise elastomeric grip features. The elastomeric grip features of the handle may be utilized to overmold, at least in part, a portion of an electrical component or a plurality thereof In such embodiments, these components may be in electrical communication via wiring which can similarly be overmolded. The elastomeric grip features may include portions which are positioned for gripping by the palm of the user and/or portions which are positioned for gripping by the thumb and index finger of the user. These elastomeric grip features may be composed of the same material or may be different, e.g. color, shape, composition, hardness, the like, and/or combinations thereof.

The refills described herein may be any suitable material. Some examples of suitable material include. polyoxymethylene (POM), polyamide (PA), polybutylene terephthalate (PBT), polypropylene (PP), acrylonitrile butadiene styrene (ABS), the like, and/or combinations thereof. In some embodiments, the refill housing may comprise a first material while the contact element carrier comprises a second material. The first material and the second material may be different.

Additionally, as used herein, the term "contact elements" is used to refer to any suitable element which can be inserted into the oral cavity. Some suitable elements include bristle tufts, elastomeric cleaning elements, elastomeric massage elements, massage elements, tongue cleaners, soft tissue cleaners, hard surface cleaners, combinations thereof, and the like. The head may comprise a variety of contact elements. For example, the head may comprise bristles, abrasive elastomeric elements, elastomeric elements in a particular orientation or arrangement, e.g. pivoting fins, prophy cups, or the like. Some suitable examples of elastomeric cleaning elements and/or massaging elements are described in U.S. Patent Application Publication Nos. 2007/0251040; 2004/0154112; 2006/0272112; and in U.S. Pat. Nos. 6,553,604; 6,151,745. The cleaning elements may be tapered, notched, crimped, dimpled, or the like. Some suitable examples of these cleaning elements and/or massaging elements are described in U.S. Pat. Nos. 6,151,745; 6,058,541; 5,268,005; 5,313,909; 4,802,255; 6,018,840; 5,836,769; 5,722,106; 6,475,553; and U.S. Patent Application Publication No. 2006/0080794.

The contact elements may be attached to the head in any suitable manner. Conventional methods include stapling, anchor free tufting, and injection mold tufting. For those contact elements that comprise an elastomer, these elements may be formed integral with one another, e.g. having an integral base portion and extending outward therefrom.

The head may comprise a soft tissue cleanser constructed of any suitable material. Some examples of suitable material include elastomeric materials; polypropylene, polyethylene, etc; the like, and/or combinations thereof. The soft tissue cleanser may comprise any suitable soft tissue cleansing elements. Some examples of such elements as well as configurations of soft tissues cleansers on a toothbrush are described in U.S. Patent Application Nos. 2006/0010628; 2005/0166344; 2005/0210612; 2006/0195995; 2008/0189888; 2006/0052806; 2004/0255416; 2005/0000049; 2005/0038461; 2004/0134007; 2006/0026784; 20070049956; 2008/0244849; 2005/0000043; 2007/140959; and U.S. Pat. Nos. 5,980,542; 6,402,768; and 6,102,923.

For those embodiments which include an elastomeric element on a first side of the head and an elastomeric element on a second side of the head (opposite the first), the elastomeric elements may be integrally formed via channels or gaps which extend through the material of the head. These channels or gaps can allow elastomeric material to flow through the head during an injection molding process such that both the elastomeric elements of the first side and the second side may be formed in one injection molding step.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A personal care device comprising:
    a handle having an engagement portion;
    a direct drive system disposed within the handle including a drive shaft reciprocating in a direction generally parallel to a longitudinal axis of the handle;
    a personal care attachment comprising a housing attached to the engagement portion, contact element carrier and a drive member having a proximal end and a distal end, the proximal end having an attachment element, the contact element carrier being movably coupled to the housing and the drive member reciprocating in a direction generally parallel to a longitudinal axis of the personal care attachment; and
    a plurality of contact elements being arranged on the contact element carrier, wherein the personal care attachment is driven at a frequency of between about 150 Hz to about 175 Hz and has a sound intensity level of less than about 75 dB (A);
wherein the attachment element includes a permanent magnet or a magetizable element; and wherein the personal care attachment has a resonance frequency which is at least 125 percent of the driving frequency of the personal care attachment.

2. The personal care device of claim 1, wherein the personal care attachment is unloaded.

3. The personal care device of claim 1, wherein the personal care attachment is loaded at 2 N.

4. The personal care device of claim 1, wherein the personal care device comprises a toothbrush and wherein the personal care attachment comprise a refill.

5. The personal care device of claim 4, wherein the contact element carrier is rotatably coupled to the housing.

6. The personal care device of claim 5, wherein the refill is unloaded.

7. The personal care device of claim 5, wherein the refill is loaded at 2 N.

\* \* \* \* \*